US012778759B2

(12) United States Patent
Ginn et al.

(10) Patent No.: US 12,778,759 B2
(45) Date of Patent: Nov. 3, 2026

(54) MULTI-MEMBER BONE STRUCTURE PROSTHESES

(71) Applicant: Tenon Medical, Inc., Los Gatos, CA (US)

(72) Inventors: Richard S Ginn, Gilroy, CA (US); Richard Brown, Colorado Springs, CO (US)

(73) Assignee: Tenon Medical, Inc., Los Gatos, CA (US)

( * ) Notice: Subject to any disclaimer, the term of this patent is extended or adjusted under 35 U.S.C. 154(b) by 1015 days.

(21) Appl. No.: 17/972,785

(22) Filed: Oct. 25, 2022

(65) Prior Publication Data

US 2023/0037755 A1 Feb. 9, 2023

Related U.S. Application Data

(63) Continuation-in-part of application No. 17/833,960, filed on Jun. 7, 2022, now Pat. No. 12,582,528, which (Continued)

(51) Int. Cl.
*A61F 2/30* (2006.01)
*A61B 5/055* (2006.01)

(Continued)

(52) U.S. Cl.
CPC .......... *A61F 2/30988* (2013.01); *A61B 5/055* (2013.01); *A61B 5/062* (2013.01);

(Continued)

(58) Field of Classification Search
CPC ........ A61F 2/30988; A61F 2002/30995; A61F 2/44; A61F 2/4405; A61F 2/4455; A61F 2002/448; A61F 2002/4485; A61F 2002/30123; A61F 2002/30166; A61F 2002/30385; A61F 2002/30387; A61F 2002/30878; A61F 2002/30879; A61F 2002/30883

See application file for complete search history.

(56) References Cited

U.S. PATENT DOCUMENTS 5,397,364 A * 3/1995 Kozak .................. A61B 17/025 606/247
6,468,311 B2 * 10/2002 Boyd ........................ A61F 2/28 623/17.11

(Continued)

FOREIGN PATENT DOCUMENTS

WO WO-2022/125619 A1 6/2022

*Primary Examiner* — Lynnsy M Summitt
(74) *Attorney, Agent, or Firm* — Francis Law Group

(57) ABSTRACT

A multi-member prosthesis including first and second elongated members and a central member, said multi-member prosthesis adapted to be advanced into a pilot SI joint opening in said dysfunctional SI joint via a posterior approach, the pilot SI joint opening comprising a sacrum opening and an ilium opening and a sacrum opening. The first elongated member adapted to be press-fit into the sacrum opening and the second elongated member adapted to be press-fit into the ilium opening. The central member including first and second elongated member securing means adapted to secure the first and second elongated members thereto.

12 Claims, 30 Drawing Sheets

Related U.S. Application Data is a continuation-in-part of application No. 17/833,098, filed on Jun. 6, 2022, now Pat. No. 12,551,348, which is a continuation of application No. 17/749,199, filed on May 20, 2022, now Pat. No. 12,465,491, which is a continuation-in-part of application No. 17/740,568, filed on May 10, 2022, now Pat. No. 12,472,069, which is a continuation-in-part of application No. 17/463,779, filed on Sep. 1, 2021, now Pat. No. 12,427,027, which is a continuation-in-part of application No. 13/857,977, filed on Apr. 5, 2013, now Pat. No. 11,273,042, which is a continuation of application No. 13/192,289, filed on Jul. 27, 2011, now abandoned.

(60) Provisional application No. 61/368,233, filed on Jul. 27, 2010.

(51) Int. Cl.

| | |
|---|---|
| ***A61B 5/06*** | (2006.01) |
| ***A61B 6/00*** | (2006.01) |
| ***A61B 6/03*** | (2006.01) |
| ***A61B 8/08*** | (2006.01) |
| ***A61B 17/16*** | (2006.01) |
| ***A61B 17/70*** | (2006.01) |
| ***A61B 17/88*** | (2006.01) |
| ***A61B 34/20*** | (2016.01) |
| ***A61F 2/44*** | (2006.01) |
| ***A61F 2/46*** | (2006.01) |

(52) U.S. Cl.

CPC .............. *A61B 6/032* (2013.01); *A61B 6/485* (2013.01); *A61B 8/0841* (2013.01); *A61B 17/1604* (2013.01); *A61B 17/1664* (2013.01); *A61B 17/1671* (2013.01); *A61B 17/70* (2013.01); *A61B 17/7055* (2013.01); *A61B 17/7074* (2013.01); *A61B 17/8858* (2013.01); *A61B 34/20* (2016.02); *A61F 2/4455* (2013.01); *A61F 2/4601* (2013.01); *A61F 2/4611* (2013.01); *A61B 2576/00* (2013.01); *A61F 2002/30121* (2013.01); *A61F 2002/30123* (2013.01); *A61F 2002/30166* (2013.01); *A61F 2002/30593* (2013.01); *A61F 2002/30995* (2013.01)

(56) References Cited

U.S. PATENT DOCUMENTS

| | | | | |
|---|---|---|---|---|
| 6,558,424 | B2 * | 5/2003 | Thalgott | A61F 2/4611 623/17.11 |
| 7,056,341 | B2 * | 6/2006 | Crozet | A61B 17/861 623/17.11 |
| 7,267,690 | B2 * | 9/2007 | Felt | A61F 2/442 623/17.11 |
| 7,967,866 | B2 * | 6/2011 | Dewey | A61F 2/44 606/90 |
| 8,157,865 | B2 * | 4/2012 | Hochschuler | A61F 2/4455 606/279 |
| 8,177,785 | B2 * | 5/2012 | Vaidya | A61B 17/68 606/86 R |
| 8,287,572 | B2 * | 10/2012 | Bae | A61F 2/447 606/279 |
| 8,808,377 | B2 * | 8/2014 | Donner | A61F 2/4455 623/17.11 |
| 8,951,254 | B2 * | 2/2015 | Mayer | A61B 17/1617 623/18.11 |
| 9,204,973 | B2 * | 12/2015 | Aflatoon | A61F 2/447 |
| 9,254,130 | B2 * | 2/2016 | Hollis | A61B 17/68 |
| 9,254,198 | B2 * | 2/2016 | Laurence | A61F 2/4465 |
| 9,333,090 | B2 * | 5/2016 | Donner | A61B 17/7055 |
| 9,381,045 | B2 * | 7/2016 | Donner | A61B 17/7055 |
| 9,421,109 | B2 * | 8/2016 | Donner | A61B 17/844 |
| 9,480,511 | B2 * | 11/2016 | Butters | A61F 2/4202 |
| 9,566,103 | B2 * | 2/2017 | Mayer | A61B 17/17 |
| 9,585,756 | B2 * | 3/2017 | Mayer | A61B 17/70 |
| 9,592,131 | B2 * | 3/2017 | Sandstrom | A61F 2/30767 |
| 9,615,856 | B2 * | 4/2017 | Arnett | A61B 17/0642 |
| 9,668,775 | B2 * | 6/2017 | Smith | A61B 17/7082 |
| 9,700,356 | B2 * | 7/2017 | Donner | A61B 17/86 |
| 9,737,414 | B2 * | 8/2017 | Felt | A61F 2/4465 |
| 9,757,154 | B2 * | 9/2017 | Donner | A61F 2/30988 |
| 9,788,961 | B2 * | 10/2017 | Donner | A61B 17/7055 |
| 9,801,546 | B2 * | 10/2017 | Donner | A61B 5/4528 |
| 9,826,986 | B2 * | 11/2017 | Donner | A61B 17/7055 |
| 9,877,760 | B2 * | 1/2018 | Ehler | A61B 17/846 |
| 9,888,911 | B2 * | 2/2018 | Siegal | A61B 17/025 |
| 9,907,669 | B2 * | 3/2018 | Faulhaber | A61F 2/4455 |
| 10,166,022 | B2 * | 1/2019 | Early | A61B 17/0642 |
| 10,238,382 | B2 | 3/2019 | Terrill et al. | |
| 10,245,087 | B2 * | 4/2019 | Donner | A61B 17/808 |
| 10,278,742 | B2 * | 5/2019 | Pavlov | A61F 2/447 |
| 10,376,206 | B2 * | 8/2019 | Sand | A61B 5/4851 |
| 10,376,367 | B2 * | 8/2019 | Fallin | A61B 17/8004 |
| 10,376,379 | B2 * | 8/2019 | Songer | A61F 2/4455 |
| 10,596,004 | B2 * | 3/2020 | Donner | A61B 17/1626 |
| 10,603,055 | B2 * | 3/2020 | Donner | A61B 17/1739 |
| 10,751,188 | B2 * | 8/2020 | Guo | A61B 17/7032 |
| 11,147,675 | B2 | 10/2021 | Ginn et al. | |
| 11,172,939 | B2 * | 11/2021 | Donner | A61B 17/1739 |
| 11,234,830 | B2 * | 2/2022 | Mesiwala | A61B 17/866 |
| 11,331,504 | B2 * | 5/2022 | Rennich | A61B 17/866 |
| 11,752,011 | B2 * | 9/2023 | Stuart | A61F 2/447 623/17.11 |
| 11,850,163 | B2 * | 12/2023 | Dewey | A61F 2/4455 |
| 11,857,420 | B2 * | 1/2024 | Mullin | A61F 2/2846 |
| 11,872,141 | B2 * | 1/2024 | Lee | A61B 17/8875 |
| 11,980,552 | B2 * | 5/2024 | Castro | A61F 2/4405 |
| 12,083,026 | B2 * | 9/2024 | Reckling | A61B 17/7055 |
| 2006/0212118 | A1 * | 9/2006 | Abernathie | A61F 2/4455 623/17.11 |
| 2007/0239278 | A1 * | 10/2007 | Heinz | A61F 2/4425 623/17.15 |
| 2008/0154379 | A1 | 6/2008 | Steiner et al. | |
| 2012/0209334 | A1 * | 8/2012 | Lewis | A61B 17/8014 606/286 |
| 2012/0215315 | A1 * | 8/2012 | Hochschuler | A61F 2/4455 623/17.16 |
| 2012/0253406 | A1 * | 10/2012 | Bae | A61F 2/4611 606/279 |
| 2013/0253518 | A1 * | 9/2013 | Mitchell | A61B 17/1671 606/80 |
| 2013/0253519 | A1 * | 9/2013 | Mitchell | A61B 17/863 606/80 |
| 2013/0253595 | A1 * | 9/2013 | Zucherman | A61B 17/8635 606/305 |
| 2015/0073421 | A1 | 3/2015 | Siegal et al. | |
| 2021/0393408 | A1 | 12/2021 | Ginn | |
| 2022/0071644 | A1 * | 3/2022 | Donner | A61B 17/1604 |
| 2022/0304813 | A1 | 9/2022 | Ginn et al. | |
| 2022/0304814 | A1 * | 9/2022 | Ginn | A61F 2/30767 |
| 2023/0301665 | A1 * | 9/2023 | Aksu | A61B 17/17 |
| 2024/0180710 | A1 * | 6/2024 | Peretz | A61F 2/30988 |
| 2024/0374390 | A1 * | 11/2024 | Kowalski | A61B 17/7055 |
| 2024/0415663 | A1 * | 12/2024 | Gehrchen | A61B 17/7055 |
| 2025/0000657 | A1 * | 1/2025 | Sansur | A61B 17/8875 |
| 2025/0213367 | A1 * | 7/2025 | Hart | A61B 17/864 |
| 2025/0366996 | A1 * | 12/2025 | Geist | A61B 17/864 |

* cited by examiner

MULTI-MEMBER BONE STRUCTURE PROSTHESES

CROSS-REFERENCES TO RELATED APPLICATIONS

This application is a continuation-in-part of U.S. patent application Ser. No. 17/833,960, filed on Jun. 7, 2022, which is a continuation-in-part of U.S. patent application Ser. No. 17/833,098, filed on Jun. 6, 2022, which is a continuation of U.S. patent application Ser. No. 17/749,199, filed on May 20, 2022, which is a continuation-in-part application of U.S. patent application Ser. No. 17/740,568, filed on May 10, 2022, which is a continuation-in-part application of U.S. patent application Ser. No. 17/463,779, filed on Sep. 1, 2021, which is a continuation-in part of U.S. patent application Ser. No. 13/857,977, filed on Apr. 5, 2013, now U.S. Pat. No. 11,273,042, which is a continuation application of U.S. patent application Ser. No. 13/192,289, filed Jul. 27, 2011, now abandoned, which claims the benefit of U.S. provisional patent application Ser. No. 61/368,233, filed on Jul. 27, 2010.

FIELD OF THE INVENTION

The present invention relates to systems, apparatus and methods for treating dysfunctional bone structures. More particularly, the present invention relates to systems, apparatus and methods for treating dysfunctional sacroiliac (SI) joints and structures proximate thereto.

BACKGROUND OF THE INVENTION

As is well known in the art, the sacroiliac (SI) joint 6 comprises a diarthrodial synovial joint, which, as illustrated in FIG. 1A, is defined by the interface between the articular surfaces of the sacrum 2 and the ilium 4. Thus, the SI joint 6 is defined by (and, hence, comprises) portions of the sacrum 2 and ilium 4.

As further illustrated in FIGS. 1B-1D, the SI joint 6 generally comprises the shape of an inverted capital letter "L" (denoted "13") lying on its side (rather than a triangle), where the long arm of the inverted "L" 15 (i.e., SI joint 6) is oriented along the posterior wall of the pelvis 11 (denoted "25" in FIG. 1A) and is also oriented relatively straight through its entire course. The sacral floor (denoted "21" in FIG. 1C), which is defined by the region between the anterior sacral promontory 19*a* and the apex 19*b* of the sacrum 2, generally slopes downward and laterally at an approximately 30% grade relative to the cephalocaudal axis 27.

As illustrated in FIGS. 1B and 1C, the short arm of the inverted "L" (denoted "17") is generally oriented parallel to the transverse plane of the L5-S1 lumbosacral joint and limited superiorly by the sacral ala (denoted "23" in FIG. 1C).

The apex of the inverted "L" (denoted "29" in FIG. 1B) is positioned below the S2 segment region of the sacrum 2 (denoted "S2") proximate to the S3 segment region of the sacrum 2 (denoted "S3").

As is also well known in the art, the SI joint further comprises a SI joint dorsal recess or gap 7 that is disposed between the sacrum 2 and ilium 4 proximate the S2 segment region of the sacrum 2, as illustrated in FIG. 1D.

As is further well known in the art, the SI joint further comprises articular cartilage, i.e., hyaline and fibrocartilage, and a strong, extensive ligamentous architecture, which stabilizes the SI joint.

Generally, the articular surfaces of the sacrum 2 and the ilium 4 that define the SI joint 6 comprise cortical bone 8, which is more compact, dense and hard relative to softer trabecular bone 10, which, as further illustrated in FIG. 1A, is disposed in the interior regions of the sacrum and ilium 2, 4.

The SI Joint is distinguished from other synovial joints by the atypical articulation of the different articular surfaces of the sacrum and ilium; the articular surface of the sacrum comprising hyaline cartilage and the articular surface of the ilium comprising substantially stronger fibrocartilage.

As is further well known in the art, the primary plane of motion of the SI joint is anterior-posterior along a transverse axis. The terms often employed to describe the relative motion of the sacrum and ilium are nutation, which refers to anterior-inferior movement of the sacrum while the coccyx (denoted "3" in FIG. 1A) moves posteriorly relative to the ilium, and counternutation, which refers to posterior-superior movement of the sacrum while the coccyx moves anteriorly relative to the ilium.

In most healthy individuals, the SI joint range of motion in flexion-extension is approximately 3°, approximately 1.5° in axial rotation, and approximately 0.8° in lateral bending.

As is well established, the SI joint performs several seminal biomechanical functions. The primary functions of the SI joint are to attenuate loads exerted on the upper body and to distribute the loads to the lower extremities. The SI joint also functions as a shock absorber for loads exerted on spine.

As is also well established, the noted loads and, hence, forces exerted on the SI joint can adversely affect the biomechanical functions of the SI joint, which can, and often will, result in SI joint dysfunction—an often-overlooked musculoskeletal pathology associated with lower back pain.

Indeed, SI joint dysfunction is estimated to be the primary cause of lower back pain in 15-30% of subjects afflicted with such pain. However, lower back pain associated with SI joint dysfunction is suspected to be far more common than most healthcare providers realize, since such pain is often associated with other skeletal and musculoskeletal dysfunctions.

SI joint dysfunction, and pain associated therewith, can be caused by various SI joint abnormalities and/or disorders, including traumatic fracture dislocation of the pelvis, degenerative arthritis, sacroiliitis, i.e., an inflammation or degenerative condition of the sacroiliac joint; osteitis condensans ilii, and other degenerative conditions of the SI joint structures and associated structures.

Various non-surgical methods, such as administration of pharmacological agents, e.g., the corticosteroid prednisone, and surgical methods and devices, i.e., SI joint prostheses, have been developed and employed to treat SI joint dysfunction and the pain associated therewith.

The most common approach employed to treat SI joint dysfunctions (when non-surgical treatments fail to ameliorate pain associated therewith), at present, is SI joint stabilization, i.e., reinforcing or modulating articulation by and between the sacrum and ilium, via surgical intervention.

SI joint stabilization typically comprises surgical placement of a bone structure prosthesis proximate to or in a dysfunctional SI joint and is generally characterized by the direction of access to the dysfunctional SI joint, e.g., lateral.

Although several conventional SI joint stabilization surgical methods and associated bone structure prostheses have effectively ameliorated pain associated with SI joint dysfunction, there remains many disadvantages associated with the conventional surgical methods and associated bone structure prostheses.

A major disadvantage associated with many conventional SI joint stabilization surgical methods is that the surgeon is required to make a substantial incision in and through the skin and tissues of a subject to access the dysfunctional SI joint. Often referred to as “open surgery” methods, these surgical methods have the attendant disadvantages of requiring general anesthesia and often involve increased operative time, pain, hospitalization, and recovery time due to the extensive soft tissue damage. There is also an increased probability of post-surgical complication associated with open surgery methods, such as nosocomial infection.

Minimally-invasive systems and methods for SI joint stabilization have thus been developed to address the noted disadvantages associated with open surgery methods. Although conventional minimally-invasive SI joint stabilization systems and methods, such as the systems and methods disclosed in U.S. Pub. No. 2009/0076551 to Petersen, have garnered some success in relieving pain associated with SI joint dysfunction and have effectively addressed many of the disadvantages associated with open surgery systems and methods, there similarly remains many disadvantages associated with conventional minimally-invasive SI joint stabilization systems and methods.

A major disadvantage associated with many conventional minimally-invasive SI joint stabilization methods is that such methods are difficult to perform and the associated surgical systems often require extensive, system-specific surgical training and experience. Indeed, it has been found that, notwithstanding the level of surgical training and experience that a surgeon may possess, when such conventional minimally-invasive SI joint stabilization systems and methods are employed, there is still a substantial incidence of damage to the lumbosacral neurovascular structures proximate to the SI joint.

A further disadvantage associated with many conventional minimally-invasive SI joint stabilization systems and methods is that they comprise anterior or lateral approaches to the dysfunctional SI joint and, hence, muscles, e.g., gluteal aponeurotic fascia and gluteus medius, and ligaments are typically disrupted, and nerves and blood vessels are susceptible to damage during placement of a bone structure prosthesis in a dysfunctional SI joint.

It would thus be desirable to provide improved SI joint stabilization systems, apparatus and methods that substantially reduce or eliminate the disadvantages associated with conventional SI joint stabilization systems, apparatus and methods.

It is therefore an object of the invention to provide improved SI joint stabilization systems, apparatus and methods that substantially reduce or eliminate the disadvantages associated with conventional SI joint stabilization systems, apparatus and methods.

It is another object of the invention to provide improved minimally-invasive SI joint stabilization systems and apparatus, and methods of using same, that facilitate posterior placement and, in particular, inferior-posterior placement of bone structure prostheses in and, thereby, stabilization of dysfunctional SI joints.

It is another object of the invention to provide improved minimally-invasive SI joint stabilization systems and apparatus, including improved bone structure prostheses, which, when employed to stabilize dysfunctional SI joints, disrupt less tissue and muscles, and avoid nerves and large blood vessels.

It is another object of the invention to provide improved minimally-invasive SI joint stabilization systems and apparatus, including improved bone structure prostheses, which can be readily employed to stabilize dysfunctional SI joints.

It is another object of the invention to provide improved minimally-invasive SI joint stabilization systems and apparatus, which effectively ameliorate pain associated with SI joint dysfunction.

It is another object of the invention to provide multi-member bone structure prostheses that can readily be employed in minimally-invasive SI joint stabilization methods.

It is another object of the invention to provide multi-member bone structure prostheses that facilitate remodeling of damaged osseous tissue and regeneration of new osseous tissue and osseous tissue structures.

SUMMARY OF THE INVENTION

The present invention is directed to systems, apparatus and methods for treating dysfunctional SI joints.

In one embodiment of the invention, there is thus provided an apparatus for treating dysfunctional SI joints.

In a preferred embodiment, the multi-member bone structure prosthesis comprises a first elongated member, a second elongated member and a central member,

- the multi-member bone structure prosthesis adapted to be advanced into a pilot SI joint opening in a dysfunctional SI joint via a posterior trajectory, the pilot SI joint opening comprising an ilium opening and a sacrum opening,
- the first elongated member adapted to be press-fit into the sacrum opening,
- the second elongated member adapted to be press-fit into the ilium opening,
- the first elongated member comprising a first exterior rail section and the second elongated member comprising a second exterior rail section,
- the central member comprising a first rail slot configured and adapted to receive the first exterior rail section of the first elongated member and a second rail slot configured and adapted to receive the second exterior rail section of the second elongated member, whereby, when the first exterior rail section of the first elongated member is received in the first rail slot of the central member and the second exterior rail section of the second elongated member is received in the second rail slot of the central member, the first and second elongated members are secured to the central member,
- the central member comprising a central member proximal end and a central member distal end, the central member distal end of the central member comprising a first tapered region configured and adapted to disrupt at least articular cartilage and cortical bone associated with the dysfunctional SI joint.

In a preferred embodiment of the invention, the posterior trajectory placement of the multi-member bone structure prosthesis into the pilot SI joint opening in the dysfunctional SI joint comprises an inferior-posterior trajectory.

In a preferred embodiment, when the multi-member bone structure prosthesis is advanced into the pilot SI joint opening in the dysfunctional SI joint, the multi-member bone structure prosthesis is transfixed to the ilium and sacrum bone structures, as well as the interface therebetween.

In a preferred embodiment, the first elongated member comprises a first internal lumen that extends from the proximal end to the distal end of the first elongated member, and the second elongated member comprises a second internal lumen that extends from the proximal end to the distal end of the second elongated member.

In a preferred embodiment, the first and second internal lumens are adapted to receive an osteogenic composition therein.

In some embodiments, the osteogenic composition comprises a bone material selected from the group consisting of demineralized bone matrix, autograft bone material, allograft bone material and xenograft bone material.

In some embodiments, the osteogenic composition comprises a bone morphogenic protein (BMP) selected from the group consisting of BMP-1, BMP2a, BMP2b, BMP3, BMP4, BMP5, BMP6, BMP7 and BMP8a.

In a preferred embodiment, the first and second members further comprise a plurality of slots in communication with the first and second internal lumens, the plurality of slots configured and adapted to allow the osteogenic composition, when disposed in the first and second internal lumens, to be dispersed out of the first and second internal lumens and delivered to a dysfunctional SI joint when the multi-member bone structure prosthesis is disposed therein.

In some embodiments, the distal ends of the first and second elongated members also comprise a second tapered region.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1A:
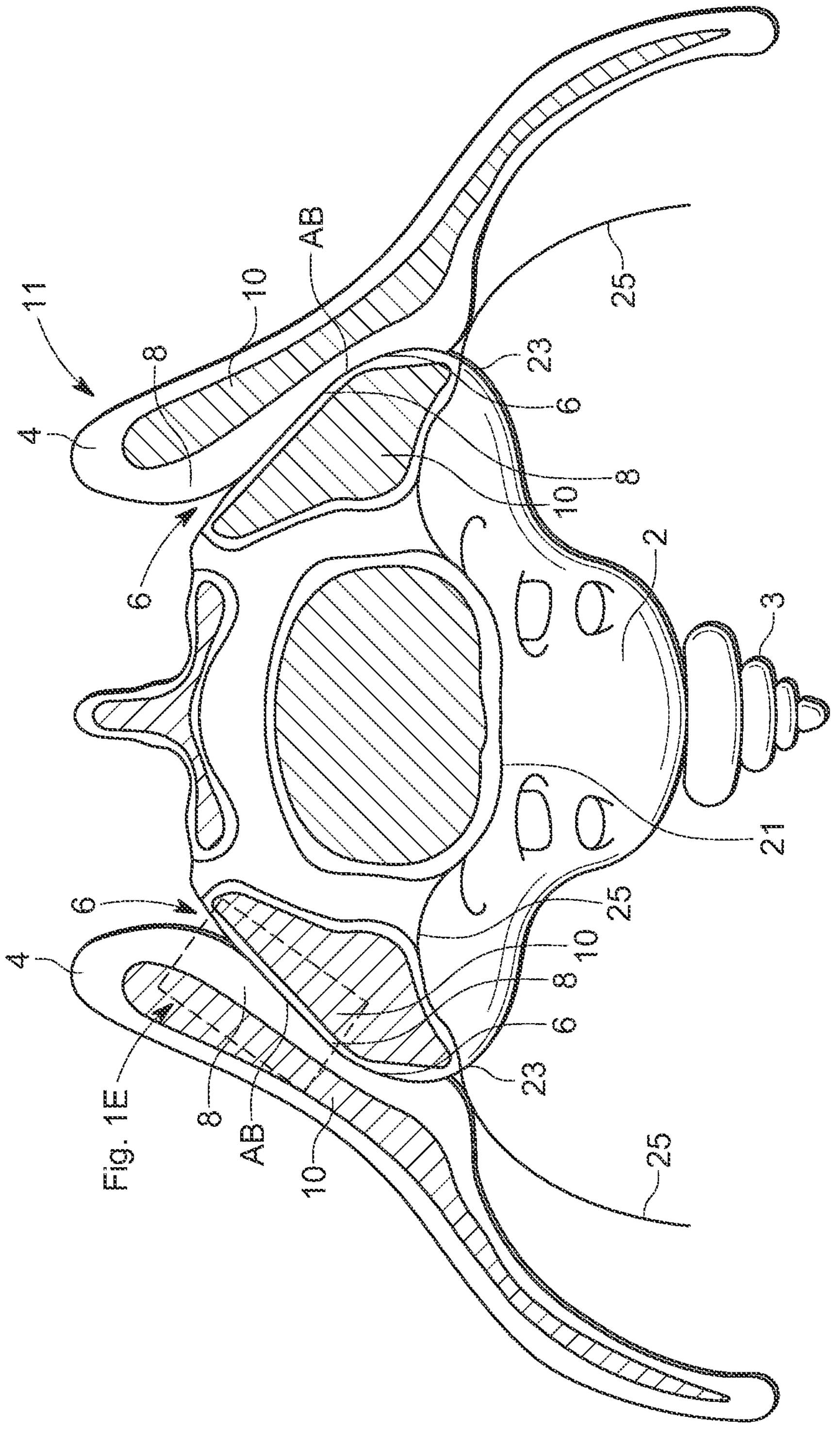
FIG. 1A is a schematic illustration of a human pelvic region from an anteroposterior (AP) perspective showing the SI joints thereof.
Figure 1B:
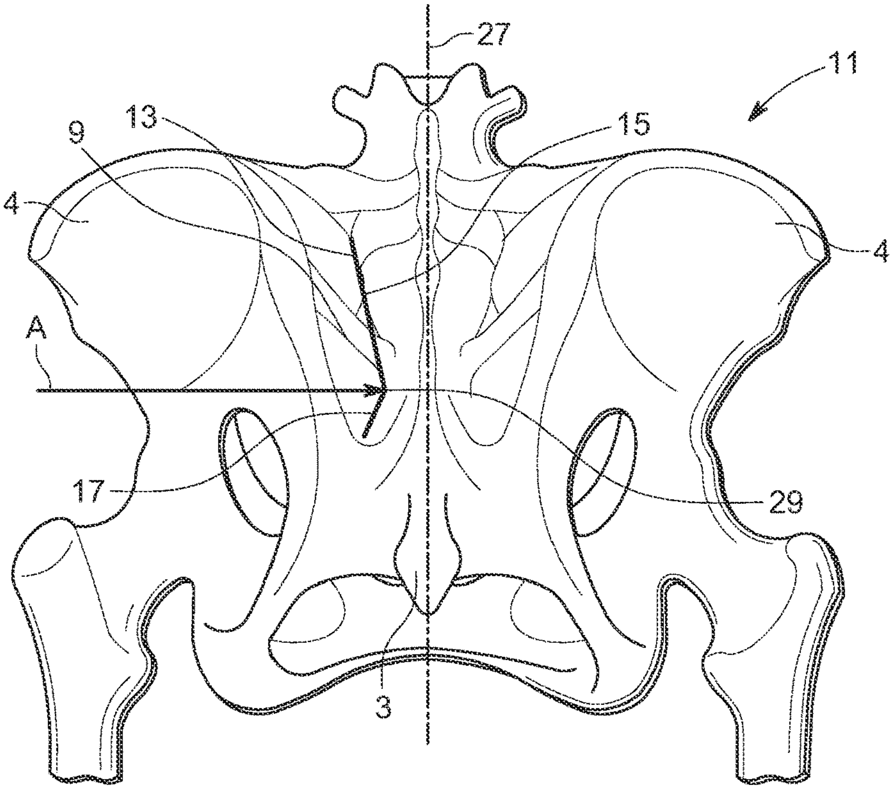
FIG. 1B is another schematic illustration of a human pelvic region from a posterior perspective showing the adjoining sacrum and ilium bone structures, and ligamentous structures thereof.

Before describing the present invention in detail, it is to be understood that this invention is not limited to particularly exemplified systems, apparatus, structures or methods as such may, of course, vary. Thus, although a number of systems, apparatus, structures and methods similar or equivalent to those described herein can be used in the practice of the present invention, the preferred systems, apparatus, structures and methods are described herein.

It is also to be understood that, although the present invention is described and illustrated in connection with sacroiliac (SI) joint stabilization, fixation and fusion procedures, the invention is not limited to such procedures. According to the invention, the systems, apparatus and methods of the invention can also be employed to stabilize and/or fuse other articulating bone structures, including, without limitation, spinal vertebrae, tarsal bones and the like.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a", "an" and "the" include plural referents unless the content clearly dictates otherwise. Thus, for example, reference to "an incision" includes two or more incisions and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "bone" and "bone structure" are used interchangeably herein, and mean and include any skeletal member or structure that comprises osseous tissue. The terms "bone" and "bone structure" thus mean and include complete and partial skeletal members or bone structures, including articulating and non-articulating bone structures, (e.g., vertebrae, sacrum, ilium, femur, etc.) and portions thereof.

The terms "sacroiliac joint", "SI joint", "sacroiliac junction" and "SI junction" are used interchangeably herein, and mean and include any region proximate to articulating regions of the sacrum and ilium bone structures and, hence, a junction between and defined by sacrum and ilium bone structures. The terms "sacroiliac joint" and "SI joint" thus mean and include a "bone" and "bone structure".

The term "dysfunctional" as used in connection with a bone structure, means and includes a physiological abnormality, disorder or impairment of a bone structure. The term "dysfunctional" as used in connection with a SI joint thus means and includes, without limitation, a traumatic fracture dislocation of the pelvis, degenerative arthritis, sacroiliitis, i.e., an inflammation or degenerative condition of the SI joint; osteitis condensans ilii, and other degenerative conditions of SI joint bone structures.

The terms "fusion" and "arthrodesis" are used interchangeably herein in connection with bone structures, and mean and include partial or complete immobilization of adjacent bone structures.

The term "stabilization", as used herein, means and includes reinforcing bone structures or sections thereof, e.g., modulating motion of adjacent articular bone structures; particularly, the sacrum and ilium bone structures. The term "stabilization", thus, in some instances, means and includes fusion and arthrodesis of adjacent bone structures.

The term "prosthesis", as used herein in connection with bone structures, means and includes a system or apparatus configured and adapted to stabilize bone structures. The term "prosthesis" thus includes a system or apparatus adapted to modulate motion of articulating bone structures; particularly, sacrum and ilium bone structures.

The term "inferior-posterior", as used herein in connection with the trajectory of a single-member and multi-member bone structure prosthesis of the invention to a SI joint, means a posterior trajectory to a SI joint through the axial and sagittal planes of the ilium and sacrum bone structures and lower than the dorsal recess of the joint.

The term "transfixed", as used herein in connection with the single-member and multi-member bone structure prostheses of the invention, means engagement of the bone structure prostheses to the ilium and sacrum bone structures, and the interface or joint therebetween.

The term "biodegradable", as used herein, means the ability of a material; particularly, a polymer or adhesive, to breakdown and be absorbed within the physiological environment of a SI joint and/or a structure associated therewith, including sacrum and ilium bone structures, by one or more physical, chemical, or cellular processes.

Biodegradable polymers, according to the invention, thus include, without limitation, polylactide polymers (PLA), copolymers of lactic and glycolic acids, including poly (lactic-co-glycolic) acid (PLGA) and poly(ε-caprolactone-co-L-lactic) acid (PCL-LA); glycine/PLA co-polymers, polyethylene oxide (PEO)/PLA block copolymers, acetylated polyvinyl alcohol (PVA)/polycaprolactone copolymers, poly(glycerol sebacate) (PGS) and its derivatives, including poly(glycerol-co-sebacate acrylate) (PGSA); poly (polyol sebacate) (PPS), poly(xylitol sebacate) (PXS), poly (xylitol glutamate sebacate) (PXGS), hydroxybutyrate-hydroxyvalerate copolymers, polyesters such as, but not limited to, aspartic acid and different aliphatic diols; poly (alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA); aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like.

Biodegradable adhesives, according to the invention, thus include, without limitation, poly(glycerol-co-sebacate acrylate) (PGSA), poly(L-glutamic acid)-based compositions, poly(γ-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol, and combinations thereof; fibrin-based compositions, collagen-based compositions, including collagen/poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and OctylSeal); poly(ethylene glycol) (PEG) based compositions, including FocalSeal®, Progel™ Duraseal™, DuraSeal™ Xact, Coseal® and ReSure Sealant; polysaccharide-based compositions, polypeptide-based compositions, and combinations thereof.

The term "osteogenic composition", as used herein, means and includes an agent or composition that induces or modulates an osteogenic physiological or biological process, or cellular activity, e.g., induces proliferation, and/or growth and/or remodeling and/or regeneration of bone or osseous tissue.

The term "osteogenic composition" thus means and includes, without limitation, the following osteogenic materials and compositions comprising same: demineralized bone matrix, autograft bone material, allograft bone material, xenograft bone material, polymethyl-methacrylate, calcium-based bone material, including hydroxyapatite (HA) and tricalcium phosphate; and combinations or mixtures thereof.

The term "osteogenic composition" also means and includes, without limitation, the following polymer materials and compositions comprising same: poly(glycerol sebacate) (PGS), poly(glycerol-co-sebacate) acrylate (PGSA) and co-polymers, such as poly(glycerol sebacate)-co-poly (ethylene glycol) (PGS-PEG); and/or composites thereof, e.g., PGS-hydroxyapatite (HA) composites and PGS-poly (ε-caprolactone) (PGS-PCL) composites.

The term "osteogenic composition" also means and includes, without limitation, acellular extracellular matrix (ECM) derived from mammalian tissue sources.

The term "osteogenic composition" thus means and includes, without limitation, acellular ECM derived from bone or osseous tissue, small intestine submucosa (SIS), epithelium of mesodermal origin, i.e., mesothelial tissue, placental tissue, omentum tissue, and combinations thereof.

The terms "biologically active agent" and "biologically active composition" are used interchangeably herein, and mean and include agent or composition that induces or modulates a physiological or biological process, or cellular activity, e.g., induces proliferation, and/or growth and/or regeneration of tissue, including osseous tissue.

The terms "biologically active agent" and "biologically active composition", as used herein, thus include agents and compositions that can be varied in kind or amount to provide a therapeutic level effective to mediate the formation or healing of osseous tissue, cartilage and connective tissue, e.g., tendons and ligaments. The term "biologically active composition", in some instances, thus means and includes an "osteogenic composition."

The terms "biologically active agent" and "biologically active composition" thus mean and include, without limitation, the following bone morphogenic proteins (BMPs) and compositions comprising same: BMP-1, BMP2a, BMP2b, BMP3, BMP4, BMP5, BMP6, BMP7 (also referred to as osteogenic protein 1 (OP-1)), and BMP8a.

The terms "biologically active agent" and "biologically active composition" also mean and include, without limitation, the following biological agents and compositions comprising same: platelet derived growth factor (PDGF), an insulin-like growth factor (IGF), including IGF-1 and IGF-2; basic fibroblast growth factor (bFGF) (also referred to as FGF2), transforming growth factor-β (TGF-β), including, TGF-β1 and TGF-β2; a growth hormone (GH), parathyroid hormone (PTH, including PTH1-34), transforming growth factor-α (TGF-α), granulocyte/macrophage colony stimulating factor (GM-CSF), epidermal growth factor (EGF), growth and differentiation factor-5 (GDF-5), vascular endothelial growth factor (VEGF), angiogenin, angiopoietin-1, del-1, follistatin, granulocyte colony-stimulating factor (G-CSF), hepatocyte growth factor/scatter factor (HGF/SF), interleukin-8 (IL-8), interleukin-10 (IL-10), leptin, midkine, placental growth factor, platelet-derived endothelial cell growth factor (PD-ECGF), platelet-derived growth factor-BB (PDGF-BB), pleiotrophin (PTN), progranulin, proliferin, a matrix metalloproteinase (MMP), angiopoietin 1 (ang1), angiopoietin 2 (ang2), and delta-like ligand 4 (DLL4).

The terms "biologically active agent" and "biologically active composition" also mean and include, without limitation, the following cells and compositions comprising same: bone marrow-derived progenitor cells, bone marrow stromal cells (BMSCs), osteoprogenitor cells, osteoblasts, osteocytes, osteoclasts, committed or partially committed cells from the osteogenic or chondrogenic lineage, hematopoietic stem cells, chondrocytes, chondrogenic progenitor cells (CPCs), mesenchymal stem cells (MSCs), and embryonic stem cells.

The terms "pharmacological agent" and "active agent" are used interchangeably herein, and mean and include an agent, drug, compound, composition or mixture thereof, including its formulation, which provides some therapeutic, often beneficial, effect. This includes any physiologically or pharmacologically active substance (or composition comprising same) that produces a localized or systemic effect or effects in animals, including warm blooded mammals.

The terms "pharmacological agent" and "active agent" thus mean and include, without limitation, the following osteoinductive agents and compositions comprising same: icaritin, tumor necrosis factor alpha (TNF-α) inhibitors, including etanercept and infliximab; disease-modifying anti-rheumatic drugs (DMARDs), including methotrexate and hydroxychloroquine; antibiotics, anti-viral agents, steroidal anti-inflammatories, non-steroidal anti-inflammatories, anti-thrombotic agents, including anti-coagulants and anti-platelet agents; and vasodilating agents.

The terms "pharmacological agent" and "active agent" further mean and include, without limitation, the following antibiotics and compositions comprising same: penicillin, carboxypenicillins, such as ticarcillin; tetracyclines, such as minocycline; gentamicin, vancomycin, ciprofloxacin, amikacin, aminoglycosides, cephalosporins, clindamycin, erythromycin, fluoroquinolones, macrolides, azolides, metronidazole, trimethoprim-sulfamethoxazole, polymyxin B, oxytetracycline, tobramycin, cefazolin, and rifampin.

The terms "anti-inflammatory" and "anti-inflammatory agent" are also used interchangeably herein, and mean and include a "pharmacological agent", which, when a therapeutically effective amount is administered to a subject, prevents or treats bodily tissue inflammation, i.e., the protective tissue response to injury or destruction of tissues, which serves to destroy, dilute, or wall off both the injurious agent and the injured tissues.

Anti-inflammatory agents thus include, without limitation, dexamethasone, betamethasone, prednisone, prednisolone, methylprednisolone sodium succinate, methylprednisolone, cortisone, ketorolac, diclofenac, and ibuprofen.

The term "pharmacological composition", as used herein, means and includes a composition comprising a "pharmacological agent" and "active agent".

The term "therapeutically effective", as used herein, means that the amount of the "pharmacological agent" and/or "pharmacological composition" and/or "biologically active agent" and/or "biologically active composition" administered is of sufficient quantity to induce a physiological reaction, preferably, a positive or desirable physiological reaction in a subject.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "one embodiment", "one aspect", and "an embodiment" and "an aspect", as used herein, means that a particular feature, structure, or characteristic described in connection with the embodiment may be included in at least one embodiment and not that any particular embodiment is required to have a particular feature, structure or characteristic described herein unless set forth in the claim.

The phrase "in one embodiment" or similar phrases employed herein do not limit the inclusion of a particular element of the invention to a single embodiment. The element may thus be included in other, or all embodiments discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present invention is directed to minimally-invasive systems, apparatus and methods for treating dysfunctional bone structures; particularly, dysfunctional SI joints.

In some embodiments of the invention, there are thus provided minimally-invasive apparatus for treating dysfunctional SI joints.

In some embodiments, the minimally-invasive apparatus comprise single-member bone structure prostheses, as set forth in Co-pending priority U.S. application Ser. No. 17/833,960.

In some embodiments, the minimally-invasive apparatus comprise multi-member bone structure prostheses.

Figure 1C:
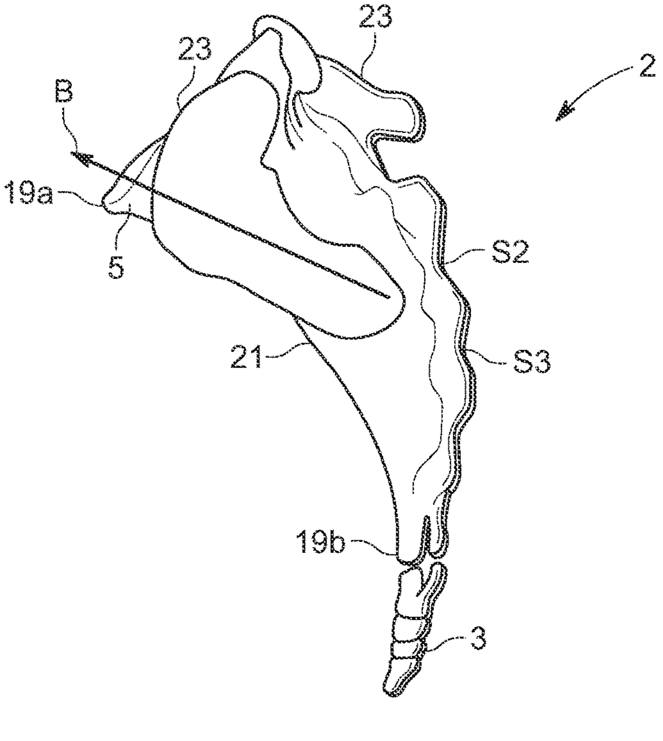
FIG. 1C is a schematic illustration of the sacrum and coccyx from a lateral perspective showing the sacral promontory and the articular surface of sacrum.
Figure 1D:
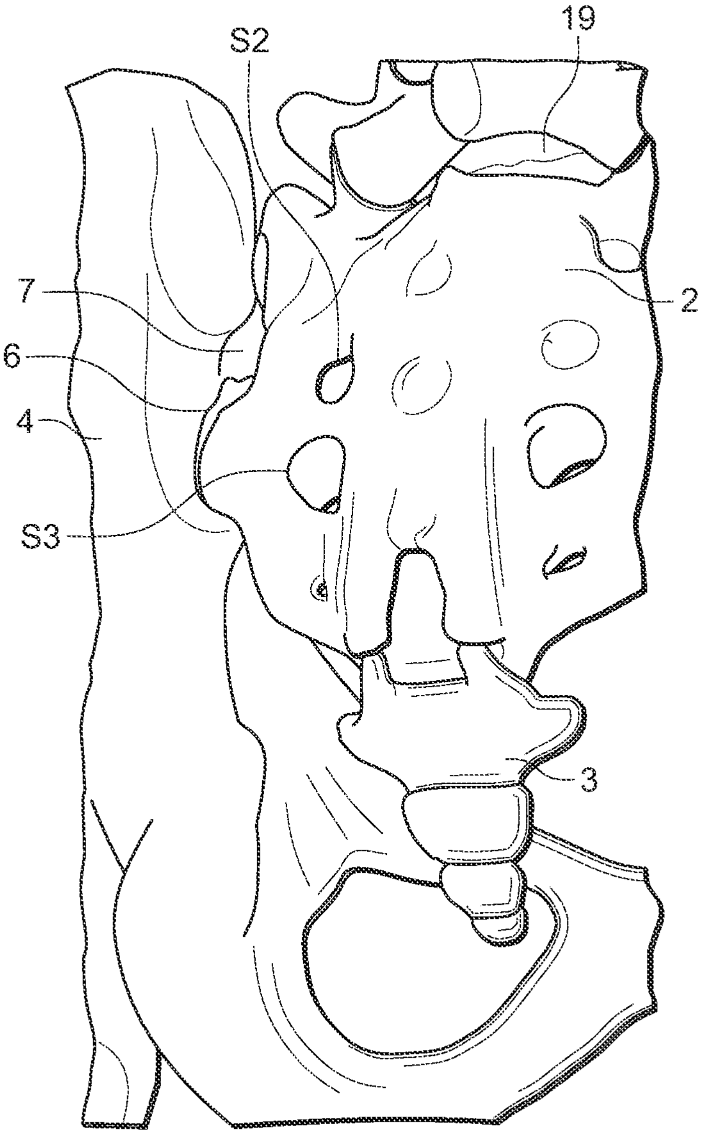
FIG. 1D is another schematic illustration of a human pelvic region from an inferior-posterior perspective showing the adjoining sacrum and ilium bone structures of an SI joint, and an SI joint dorsal recess between the sacrum and ilium bone structures.

In a preferred embodiment of the invention, the single-member and multi-member bone structure prostheses are configured and adapted to be delivered to dysfunctional SI joints via a posterior trajectory, more preferably, an inferior-posterior trajectory, such as illustrated in FIG. 1C and denoted by arrow "B", to stabilize the dysfunctional SI joints.

As indicated above, SI joint stabilization (and, hence, treatment), including minimally-invasive SI joint stabilization, typically comprises surgical placement of a bone structure prosthesis proximate to or in a dysfunctional SI joint via anterior or lateral trajectories.

From the perspective of FIG. 1A, an anterior approach to the SI joint 6 shown in FIG. 1A (and, hence, a dysfunctional SI joint) would be substantially perpendicular to the page upon which FIG. 1A is printed.

More recently, a posterior trajectory has been employed to advance a bone structure prosthesis proximate to and in a dysfunctional SI joint.

Figure 1E:
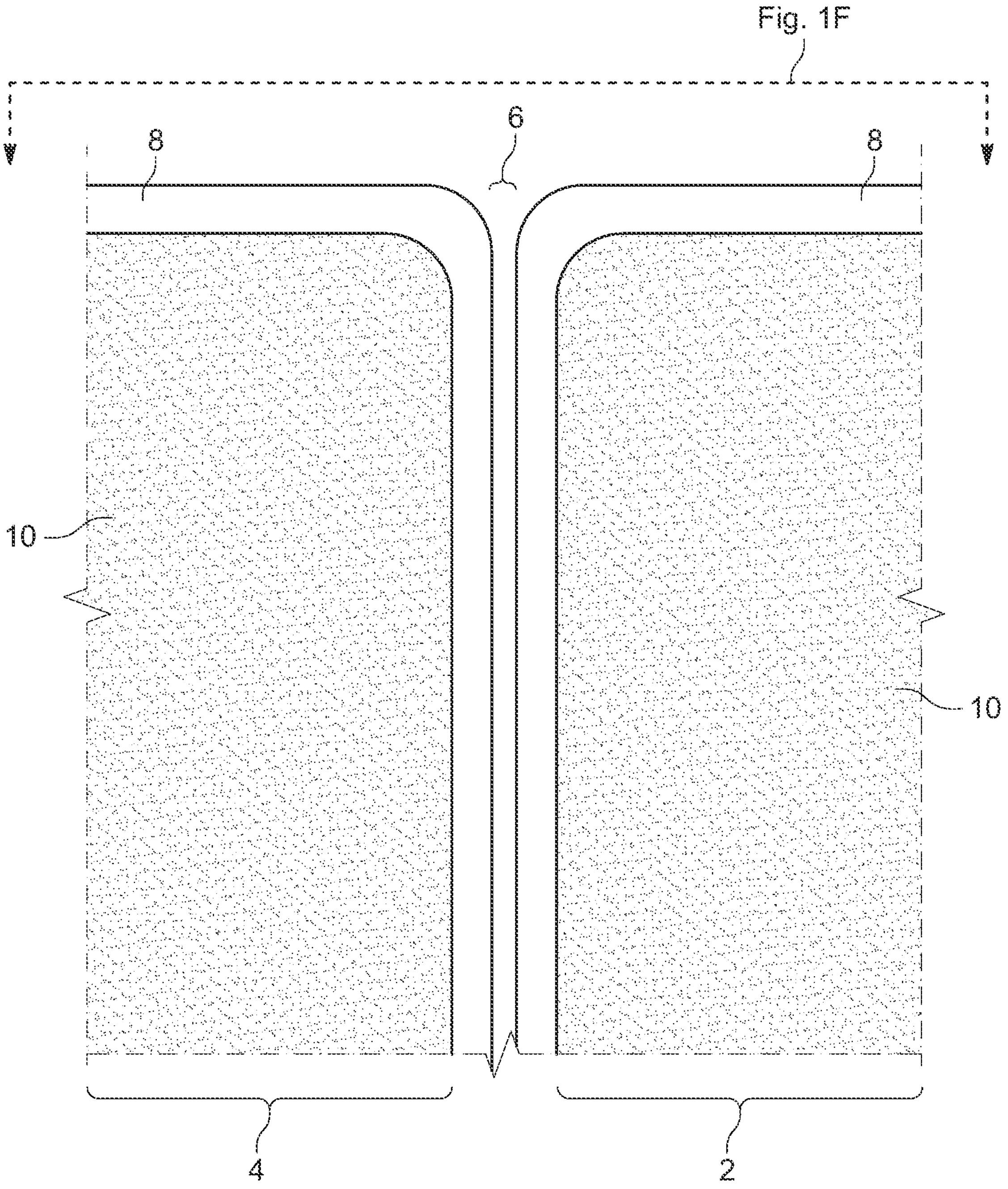
FIG. 1E is an illustration of a SI joint from a superior perspective showing the adjoining sacrum and ilium articular surfaces.

Referring to FIG. 1E there is shown an illustration of a SI joint 6 and surrounding structures. For illustrative simplicity, a uniform layer of cortical bone 8 is shown adjacent a deeper layer of trabecular bone 10 on both of the depicted sacrum 2 and ilium 4 structures. However, in actuality, such layers are far less uniform and homogeneous.

Figure 1F:
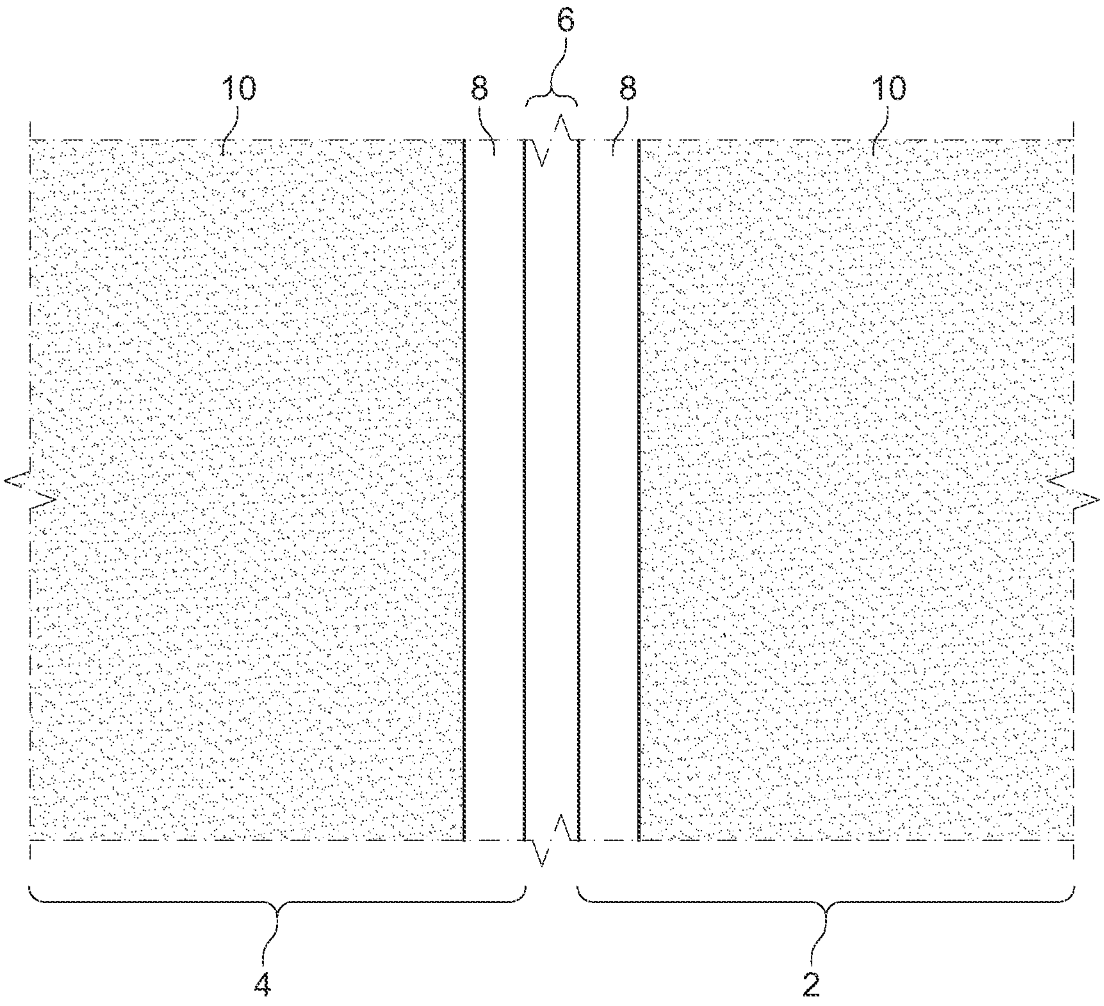
FIG. 1F is another illustration of a SI joint from a posterior perspective showing the adjoining sacrum and ilium articular surfaces.
Figure 1G:
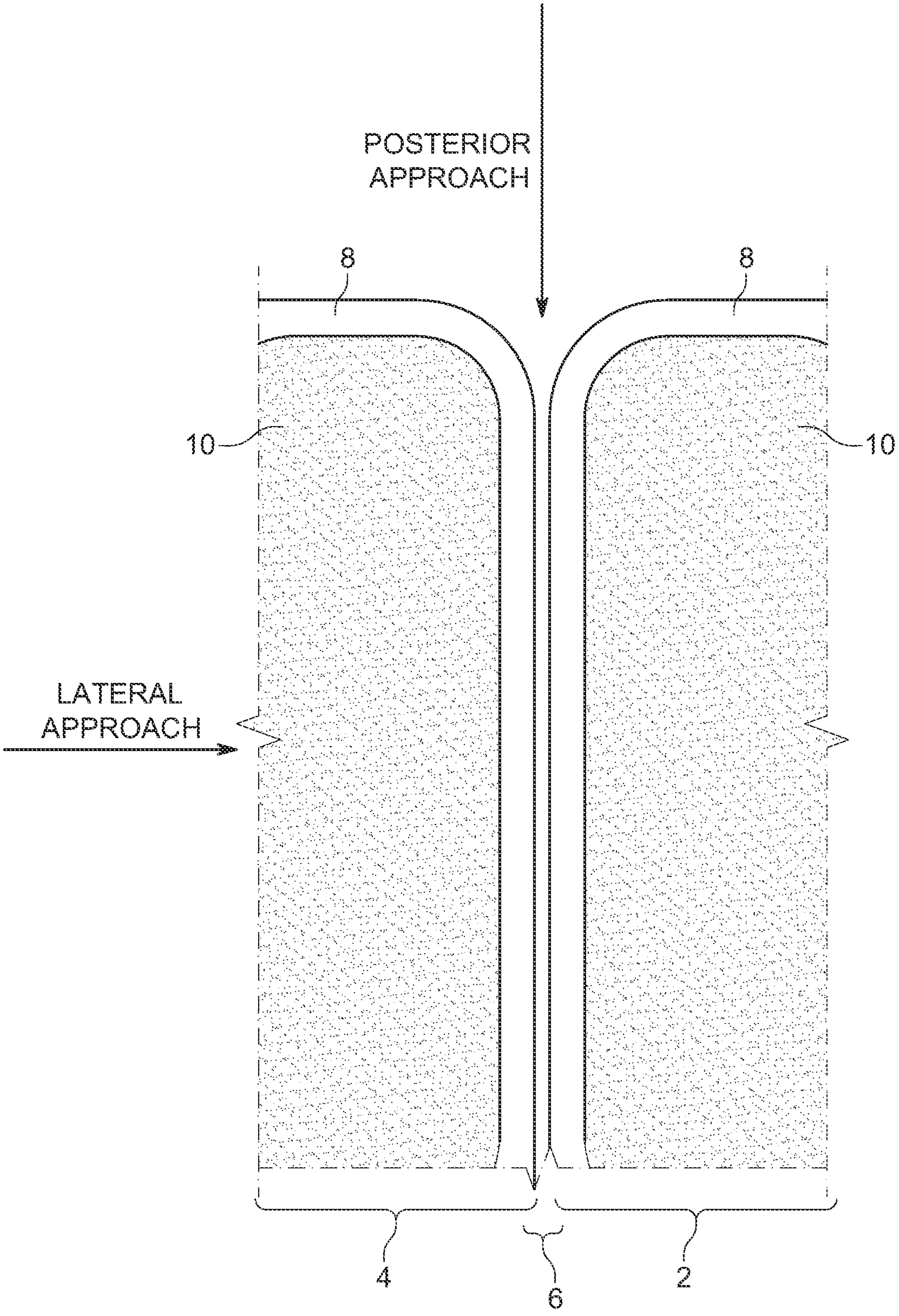
FIG. 1G is a further illustration of the SI joint shown in FIG. 1F illustrating lateral and posterior approaches to the SI joint, in accordance with the invention.

Referring now to FIG. 1F, there is shown a view of the same structure from a different posterior perspective. From the perspective of FIG. 1F, a posterior approach or trajectory to the SI joint 6 (and, hence, a dysfunctional SI joint) would be substantially perpendicular to the page upon which FIG. 1F is printed. Indeed, referring to FIG. 1G, a variation similar to that depicted in FIG. 1E is illustrated, showing an approximate approach vector for a lateral trajectory to the SI joint 6 versus a posterior trajectory, using the orientation paradigms introduced in FIGS. 1A and 1F-1G. Such paradigms are used to illustrate various embodiments of the subject invention in various figures that follow FIGS. 1A and 1F-1G.

As indicated above, a major disadvantage associated with many conventional anterior and lateral trajectories of a bone structure prosthesis to a dysfunctional SI joint is that muscles and ligaments are typically disrupted and often damaged. Nerves and blood vessels are also susceptible to damage during such SI joint stabilization methods.

In contrast, posterior delivery; particularly, inferior-posterior delivery, of the bone structure prostheses of the invention to a dysfunctional SI joint is much less invasive. Indeed, less tissue and fewer muscles are disrupted, and nerves and large blood vessels are avoided. The bone structure prostheses are also transfixed to optimal regions of cortical bone proximate a dysfunctional SI joint and, thereby, provide superior arthrodesis of the dysfunctional SI joint.

Thus, as indicated above, the single-member and multi-member bone structure prostheses of the invention are configured and adapted to be delivered to and inserted into dysfunctional SI joints via a posterior trajectory.

As discussed in detail below, in a preferred embodiment, the single-member and multi-member bone structure prostheses of the invention are configured and adapted to be delivered to and inserted into dysfunctional SI joints via an inferior-posterior trajectory.

Referring now to FIGS. 2A-2F, there are shown depictions of one embodiment of a single-member bone structure prosthesis (denoted "70") of the invention.

As set forth in Co-pending priority U.S. application Ser. No. 17/833,960 and illustrated in FIGS. 2A and 2B, the single-member bone structure prosthesis 70 comprises a biocompatible and, hence, implantable member comprising proximal and distal ends 72, 74, and first and second elongated partially cylindrical sections or pontoons 76*a*, 76*b* connected to a bridge section 78, i.e., a transfixing osteotome bridge, whereby the single-member bone structure prosthesis 70 comprises a continuous exterior surface comprising first and second partially cylindrical surface regions 77*a*, 77*b*.

Figure 2A:
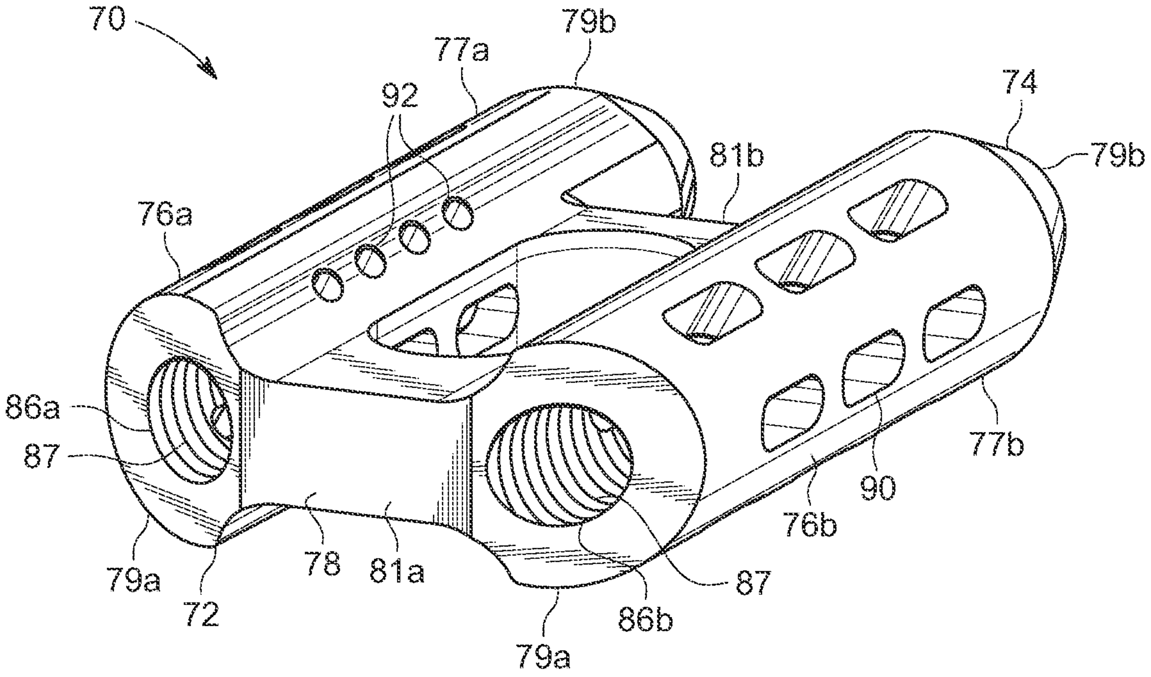
FIG. 2A is a perspective view of one embodiment of a single-member bone structure prosthesis, in accordance with the invention.
Figure 2B:
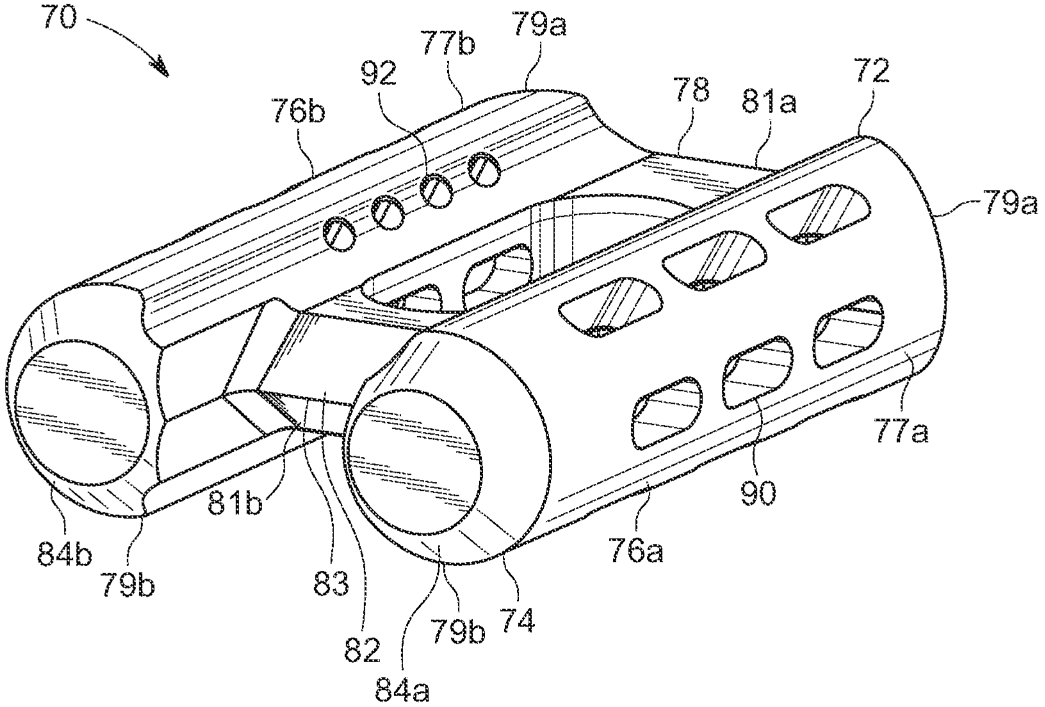
FIG. 2B is a further perspective view of the single-member prosthesis shown in FIG. 2A, in accordance with the invention.

As further illustrated in FIGS. 2A and 2B, the first and second partially cylindrical sections 76*a*, 76*b* comprise proximal and distal ends 79*a*, 79*b*. The bridge section 78 similarly comprises proximal and distal ends 81*a*, 81*b*.

As also set forth in Co-pending priority U.S. application Ser. No. 17/833,960, the single-member bone structure prosthesis 70 can comprise any suitable length from the proximal ends 79*a* to the distal ends 79*b* of the partially cylindrical sections 76*a*, 76*b*. In some embodiments, the single-member bone structure prosthesis 70 comprises a length in the range of 20-50 mm, more preferably, a length in the range of 30-40 mm.

As further set forth in Co-pending priority U.S. application Ser. No. 17/833,960, the first partially cylindrical surface region 77*a* of the first partially cylindrical section 76*a* preferably comprises a partially cylindrical surface region shape that corresponds to at least a first portion of a pilot SI joint opening in the dysfunctional SI joint, and the second partially cylindrical surface region 77*b* of the second partially cylindrical section 76*b* similarly preferably comprises a partially cylindrical surface region shape that corresponds to at least a second portion of the pilot SI joint opening in the dysfunctional SI joint.

As illustrated in FIG. 2B, the distal end 81*b* of the bridge section 78 preferably comprises a taper region 82, which is configured and adapted to disrupt, i.e., cut into and through, articular cartilage and cortical bone 8 (and, in some aspects, trabecular bone 10).

As further illustrated in FIG. 2B, the distal ends 79*b* of the first and second partially cylindrical sections 76*a*, 76*b* also preferably comprise tapered regions 84*a*, 84*b*, which facilitate insertion of the first and second elongated partially cylindrical sections 76*a*, 76*b* into dysfunctional SI joints.

Figure 2C:
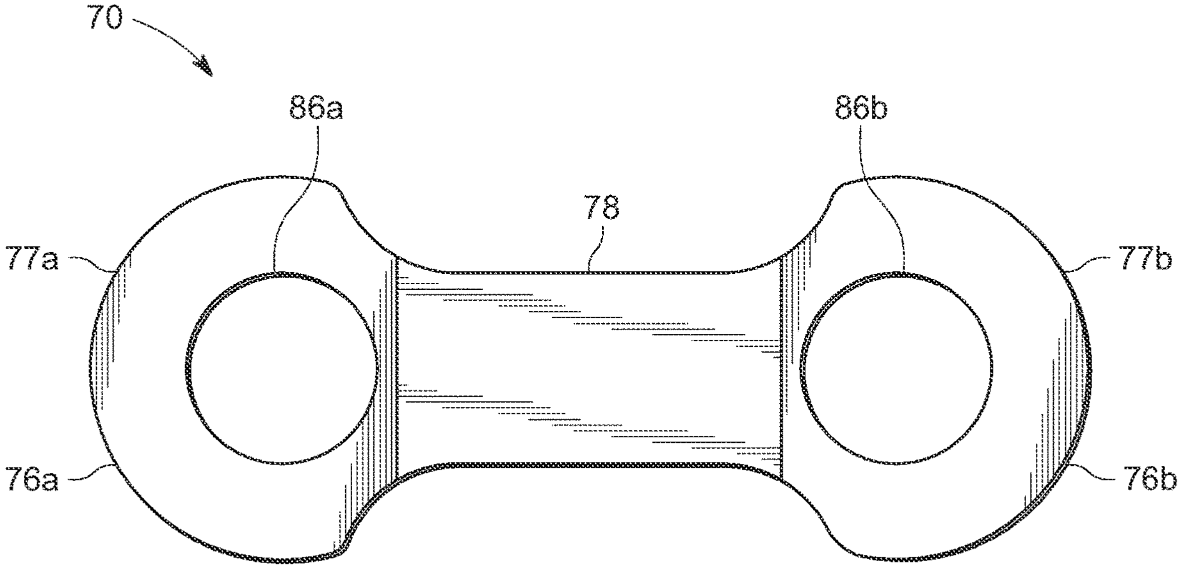
FIG. 2C is a rear plan view of the single-member prosthesis shown in FIG. 2A, in accordance with the invention.
Figure 2D:
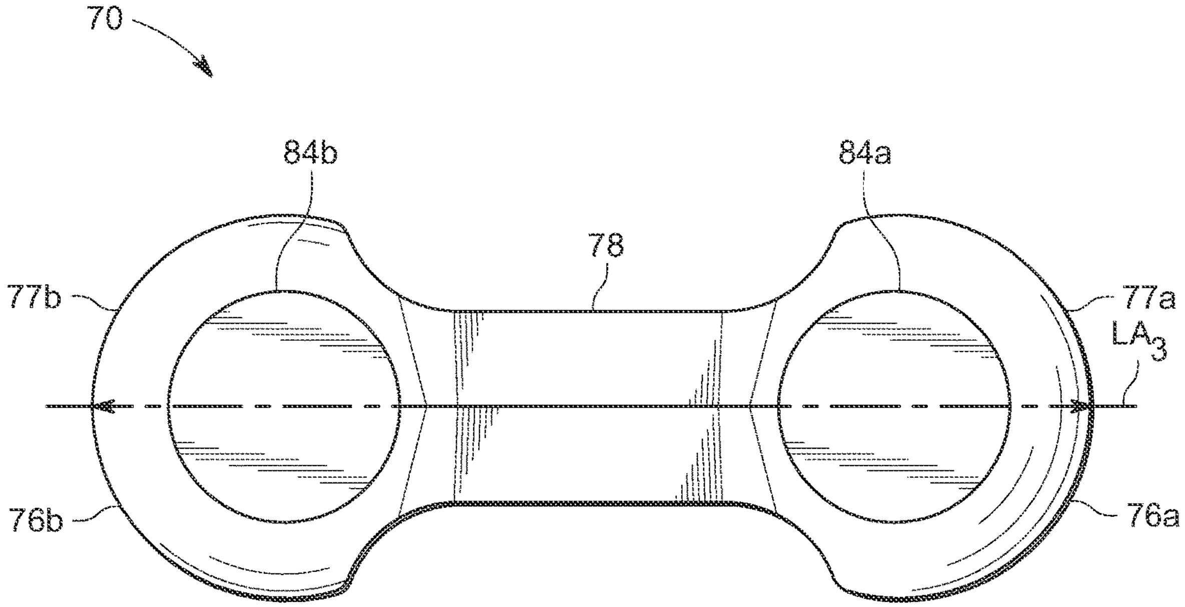
FIG. 2D is a front plan view of the single-member prosthesis shown in FIG. 2A, in accordance with the invention.
Figure 2E:
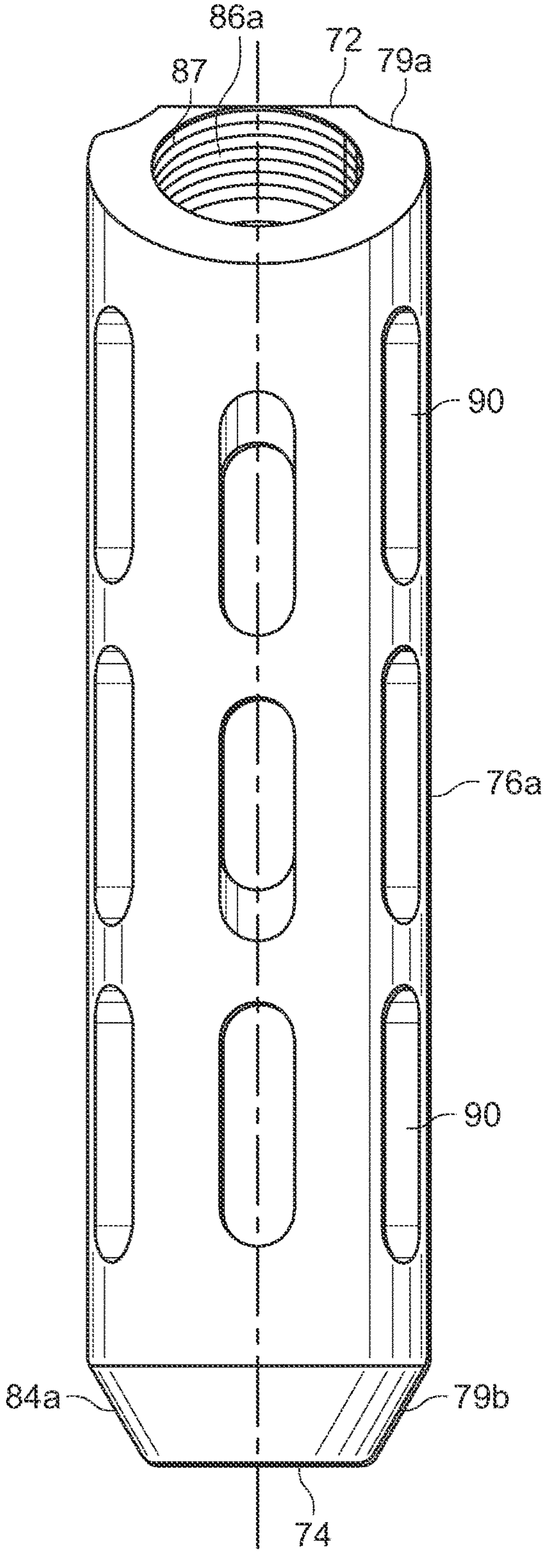
FIG. 2E is a right-side plan view of the single-member prosthesis shown in FIG. 2A, in accordance with the invention.
Figure 2F:
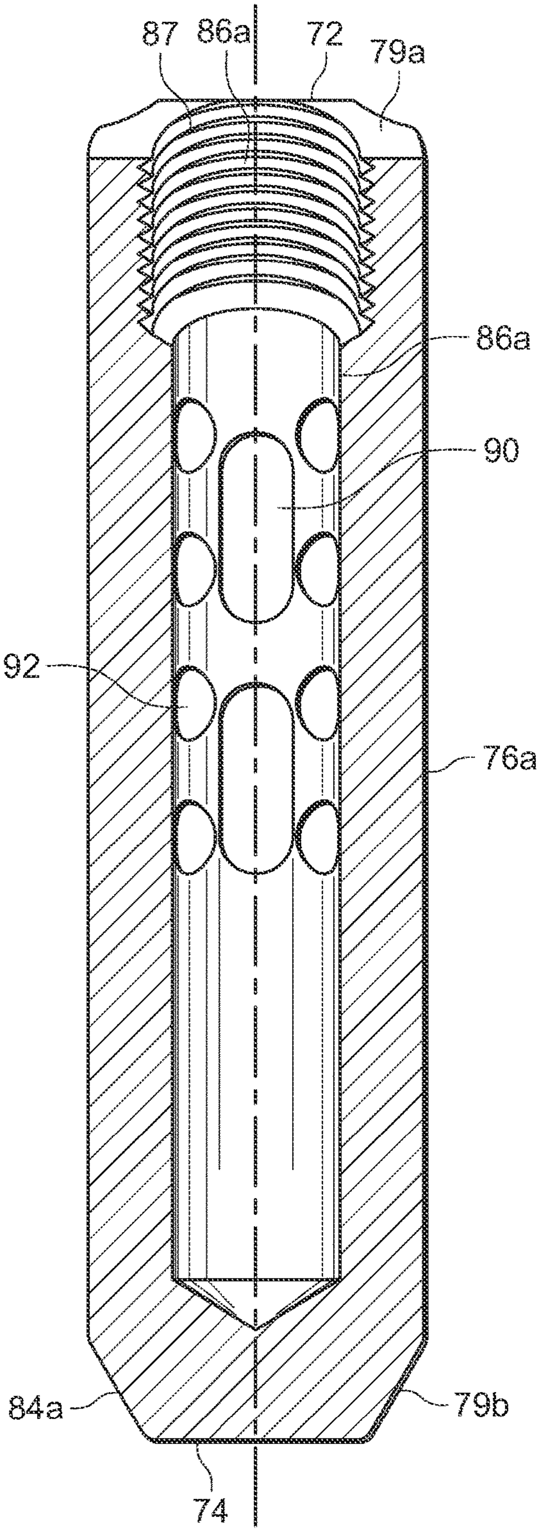
FIG. 2F is a right-side sectional plan view of the single-member prosthesis shown in FIG. 2A, in accordance with the invention.

As illustrated in FIGS. 2A, 2C, and 2F, the first and second partially cylindrical sections 76*a*, 76*b* of the single-member bone structure prosthesis 70 comprise internal prosthesis engagement member lumens 86*a*, 86*b*, respectively.

As set forth in Co-pending priority U.S. application Ser. No. 17/833,960 and further illustrated in FIG. 2A, in a preferred embodiment of the invention, the internal prosthesis engagement member lumens 86*a*, 86*b* comprise internal threaded regions 87 adapted to engage a prosthesis deployment assembly, which is adapted to advance the single-member bone structure prosthesis 70 to and into a dysfunctional SI joint.

As further set forth in Co-pending priority U.S. application Ser. No. 17/833,960, in a preferred embodiment, the internal prosthesis engagement lumens 86*a*, 86*b* are also configured to receive one or more of the aforementioned biologically active agents and compositions, including osteogenic agents and compositions, and pharmacological agents and compositions that promote or induce proliferation, and/or growth and/or remodeling and/or regeneration of osseous tissue and/or facilitate osseous tissue ingrowth into the single-member bone structure prosthesis 70 when the prosthesis 70 is disposed in a dysfunctional SI joint.

Referring back to FIGS. 2A and 2B, in a preferred embodiment, the single-member bone structure prosthesis 70 further comprises a plurality of slots 90 and apertures 92, which preferably are in communication with the internal prosthesis engagement member lumens 86*a*, 86*b*; the first and second partially cylindrical sections 76*a*, 76*b* thus comprising hollow, fenestrated members.

In a preferred embodiment, the apertures 92 are sized and configured to allow the biologically active agent compositions and/or pharmacological agent compositions to be dispersed out of the internal prosthesis engagement member lumens 86*a*, 86*b* and delivered to a dysfunctional SI joint when the single-member bone structure prosthesis 70 is disposed therein.

In a preferred embodiment, when the single-member bone structure prosthesis 70 is disposed in a SI joint, the single-member bone structure prosthesis 70 is transfixed thereto, i.e., the first partially cylindrical section 76*a* is transfixed to the ilium bone structure, the second partially cylindrical section 76*b* is transfixed to the sacrum bone structure (or vice versa), and the bridge section 78 is transfixed to the interface between the ilium and sacrum bone structures.

Referring now to FIGS. 3A-3G, there are shown depictions of one embodiment of a multi-member bone structure prosthesis (denoted "170") of the invention.

Figure 3A:
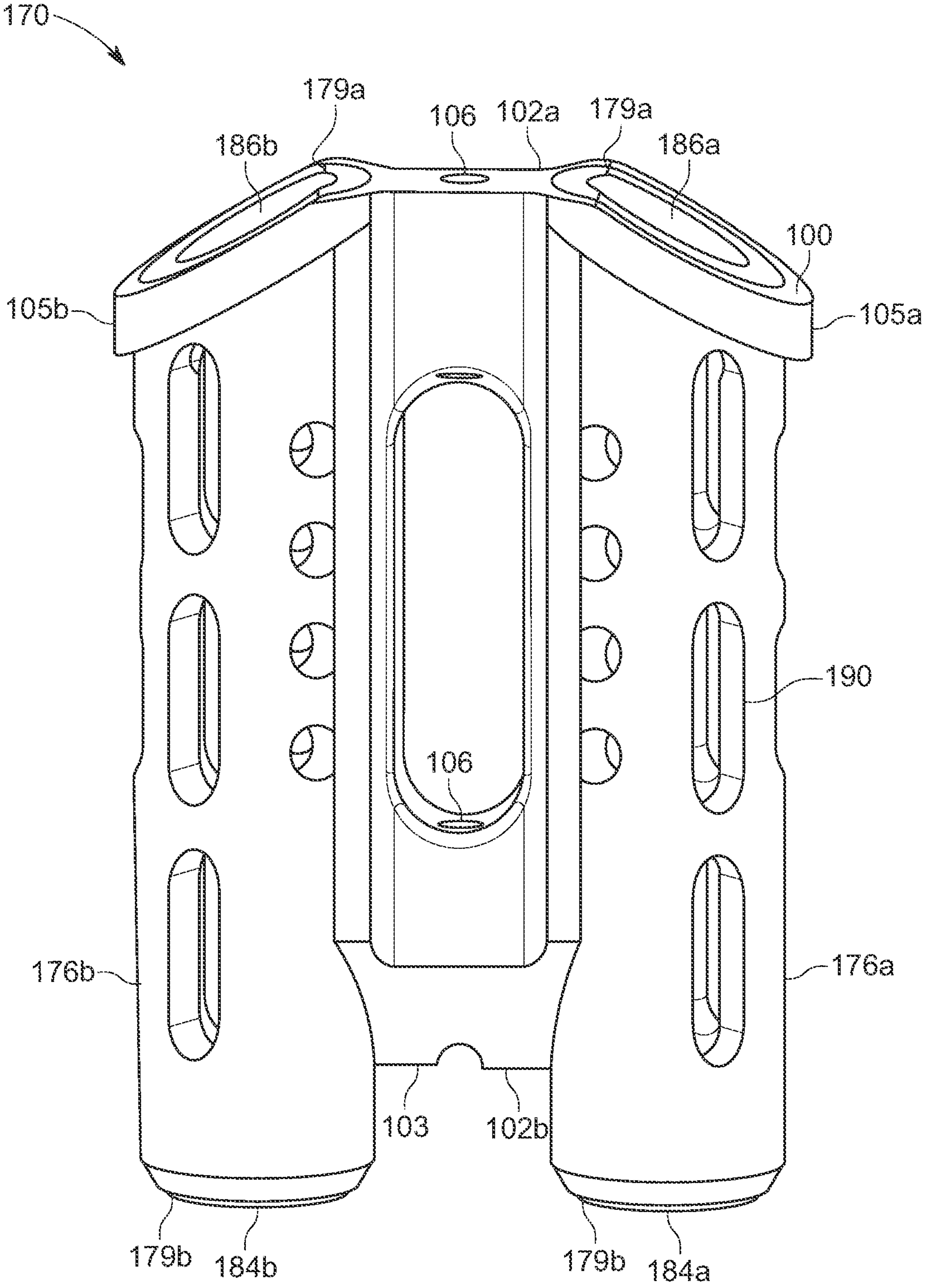
FIG. 3A is a front plan view of one embodiment of a multi-member bone structure prosthesis, in accordance with the invention.

As illustrated in FIG. 3A, the multi-member bone structure prosthesis 170 (also referred to hereinafter as a "multi-member prosthesis"), comprises a biocompatible and, hence, implantable member comprising first and second elongated members 176*a*, 176*b* and a central member 100; the central member 100 comprising proximal and distal ends 102*a*, 102*b*.

Figure 6A:
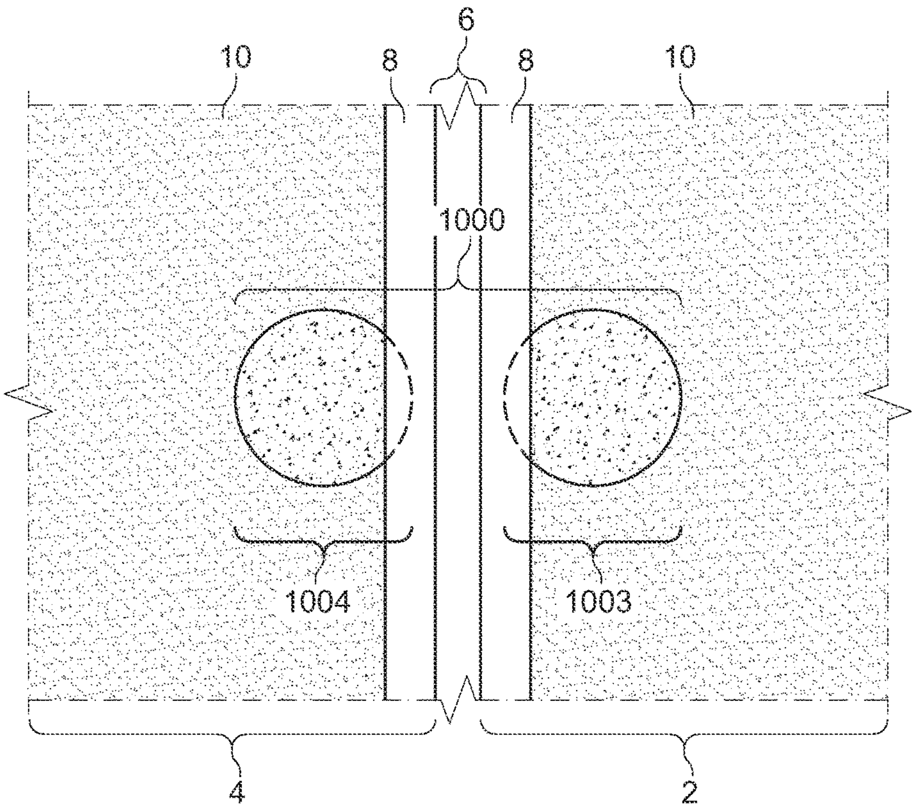
FIGS. 6A and 6B are illustrations of pilot SI joint openings that can be created with the drill guide shown in FIG. 7A, in accordance with the invention.
Figure 6B:
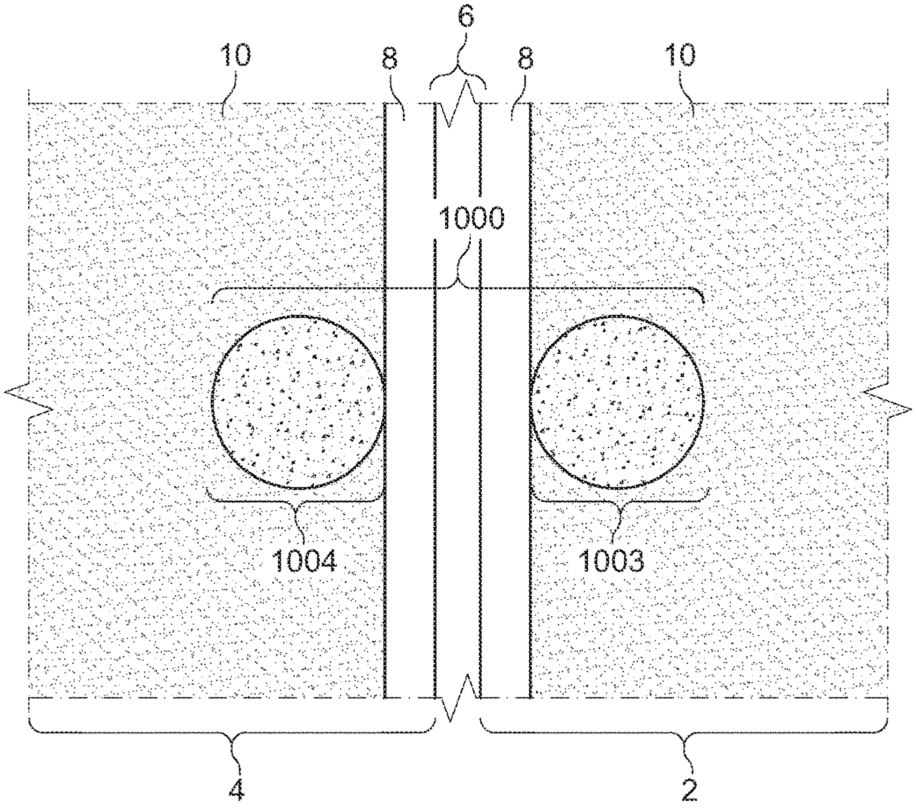

In a preferred embodiment, the first elongated member 176*a* preferably comprises a cross-sectional shape that corresponds to at least a portion of the cross-sectional shape of a first portion of a pilot SI joint opening in the dysfunctional SI joint, such as the sacrum portion 1003 of the pilot SI joint opening 1000 shown in FIGS. 6A and 6B, and the second elongated member 176*b* similarly preferably comprises a cross-sectional shape that corresponds to at least a portion of the cross-sectional shape of a second portion of the pilot SI joint opening in the dysfunctional SI joint, such as the ilium portion 1004 of the pilot SI joint opening 1000.

Figure 3B:
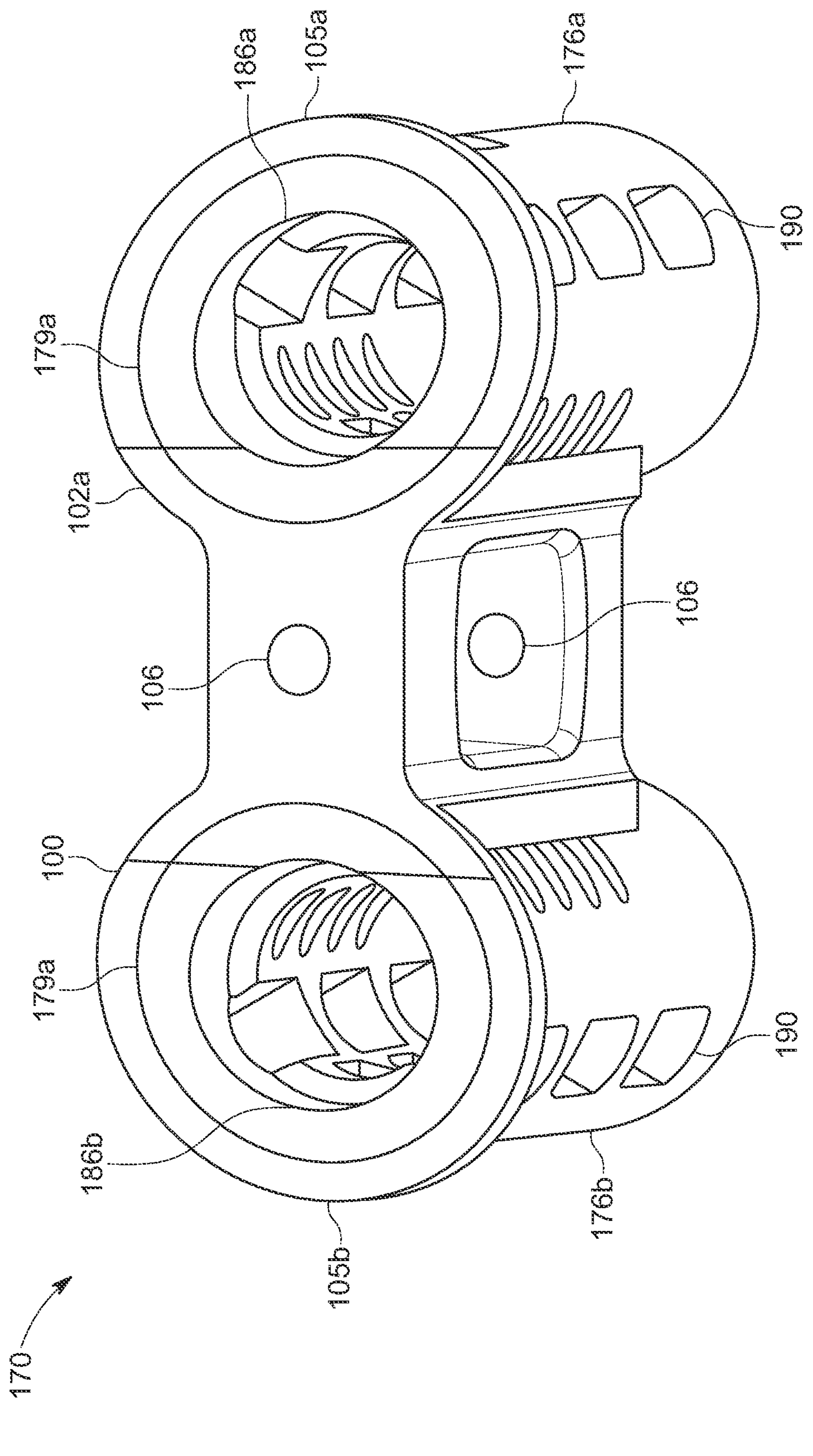
FIG. 3B is a top perspective view of the multi-member prosthesis shown in FIG. 3A, in accordance with the invention.
Figure 3C:
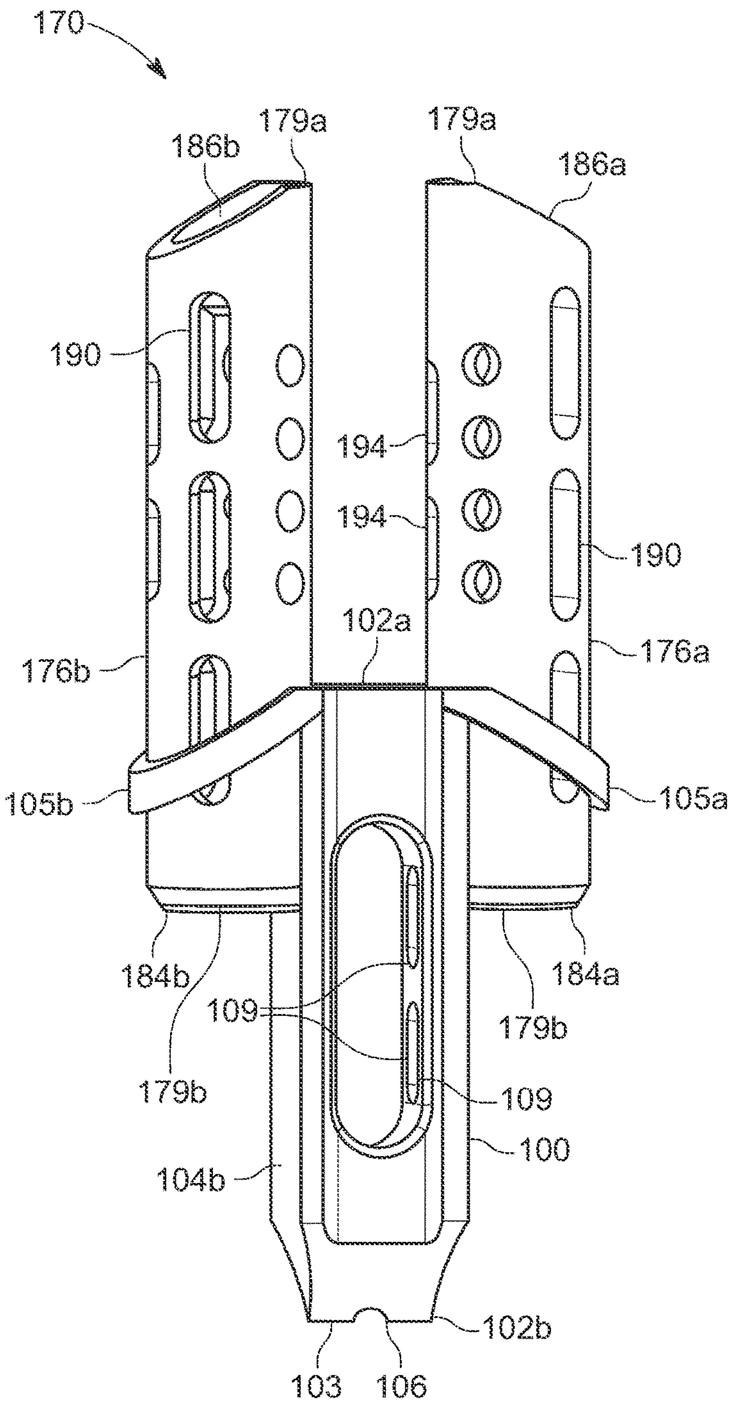
FIG. 3C is a further front plan view of the multi-member prosthesis shown in FIG. 3A illustrating the first and second elongated members of the prosthesis partially secured to the central member, in accordance with the invention.
Figure 3D:
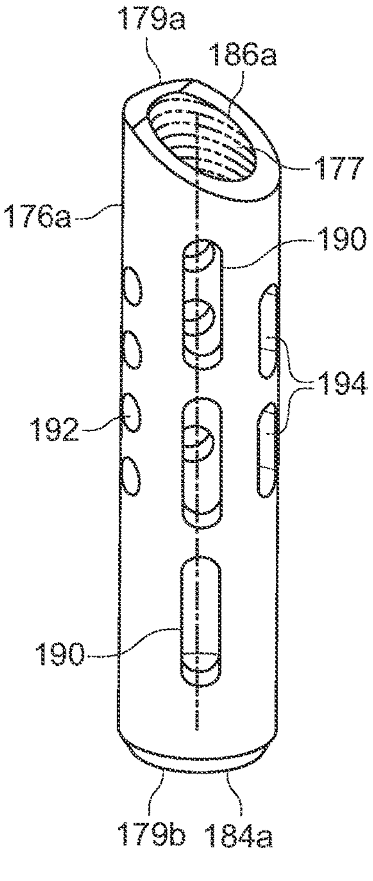
FIG. 3D is a perspective view of the right-side elongated member of the multi-member prosthesis shown in FIG. 3A, in accordance with the invention.

As illustrated in FIGS. 3A, 3B and 3D, the first and second elongated members 176*a*, 176*b* comprise proximal and distal ends 179*a*, 179*b*.

As further illustrated in FIGS. 3B and 3D, in a preferred embodiment, the first elongated member 176*a* comprises a first elongated member internal lumen 186*a* and the second elongated member 176*b* similarly comprises a second elongated member internal lumen 186*b*.

In a preferred embodiment, the distal ends 179*b* of the first and second elongated members 176*a*, 176*b* comprise closed distal ends, whereby the first and second elongated member internal lumens 186*a*, 186*b* do not extend through the distal ends 179*b* of the first and second elongated members 176*a*, 176*b*.

In a preferred embodiment, the first and second elongated member internal lumens 186*a*, 186*b* are configured to receive agents and compositions that facilitate adhesion of the first and second elongated members 176*a*, 176*b* and, hence, multi-member bone structure prosthesis 170 to and, hence, in dysfunctional SI joints. Such agents and compositions are set forth in in Co-pending U.S. application Ser. No. 17/463,831, which is incorporated by reference herein.

In a preferred embodiment, the first and second elongated member internal lumens 186*a*, 186*b* are also configured to receive one or more the aforementioned biologically active agents and compositions, including osteogenic agents and compositions, and pharmacological agents and compositions that promote or induce proliferation, and/or growth and/or remodeling and/or regeneration of osseous tissue and/or facilitate osseous tissue ingrowth into the multi-member bone structure prosthesis 170 when the prosthesis 170 is disposed in a dysfunctional SI joint.

As further illustrated in FIGS. 3A, 3C and 3D, in a preferred embodiment, the first and second elongated members 176*a*, 176*b* further comprise a plurality of slots 190, 194 and apertures 192, which preferably are in communication with the first and second elongated member internal lumens 186*a*, 186*b*; the first and second elongated members 176*a*, 176*b* thus similarly comprising hollow, fenestrated members.

In a preferred embodiment, the slots 190, 194 and apertures 192 are sized and configured to allow the adhesive compositions and/or biologically active agent compositions and/or pharmacological agent compositions to be dispersed out of the first and second elongated member internal lumens 186*a*, 186*b* and delivered to a dysfunctional SI joint when the multi-component prosthesis 170 is disposed therein.

In a preferred embodiment, when the first and second elongated members 176*a*, 176*b* of the multi-member bone structure prosthesis 170 are slidably received in the central member 100 elongated member securing means, i.e., first and second open regions 105*a*, 105*b*, as illustrated in FIG. 3A and discussed below, slots 194 are preferably aligned with slots 109 of the central member 100 to facilitate osseous tissue ingrowth into the multi-member prosthesis 170 when the prosthesis 170 is disposed in a dysfunctional SI joint.

In some embodiments of the invention, the first and second elongated member internal lumens 186*a*, 186*b* comprise internal threads (shown in phantom and denoted "177" in FIG. 3D) proximate the proximal ends 179*a*, such as internal prosthesis engagement member lumens 86*a*, 86*b* of the single-member bone structure prosthesis 70 shown in FIGS. 2E and 2F, to cooperate with a prosthesis deployment instrument that is adapted to advance the first and second elongated members 176*a*, 176*b* to and into a bone structure; particularly, bone structures that define a dysfunctional SI joint.

In a preferred embodiment, the central member 100 comprises elongated member securing means that is sized and configured to releasably receive and secure the first and second elongated members 176*a*, 176*b* to the central member 100, as illustrated in FIGS. 3A and 3C.

Figure 3E:
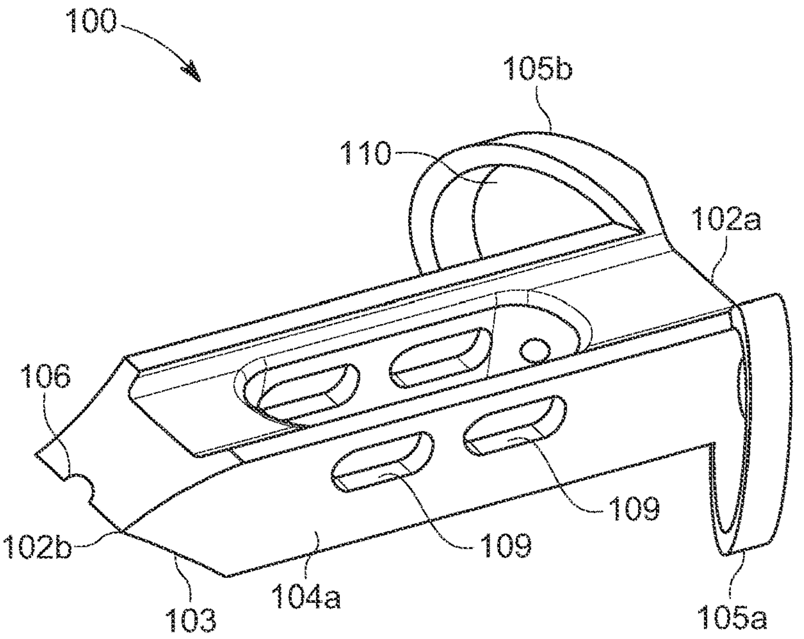
FIGS. 3E, 3F and 3G are perspective views of the central member of the multi-member prosthesis shown in FIG. 3A, in accordance with the invention.
Figure 3F:
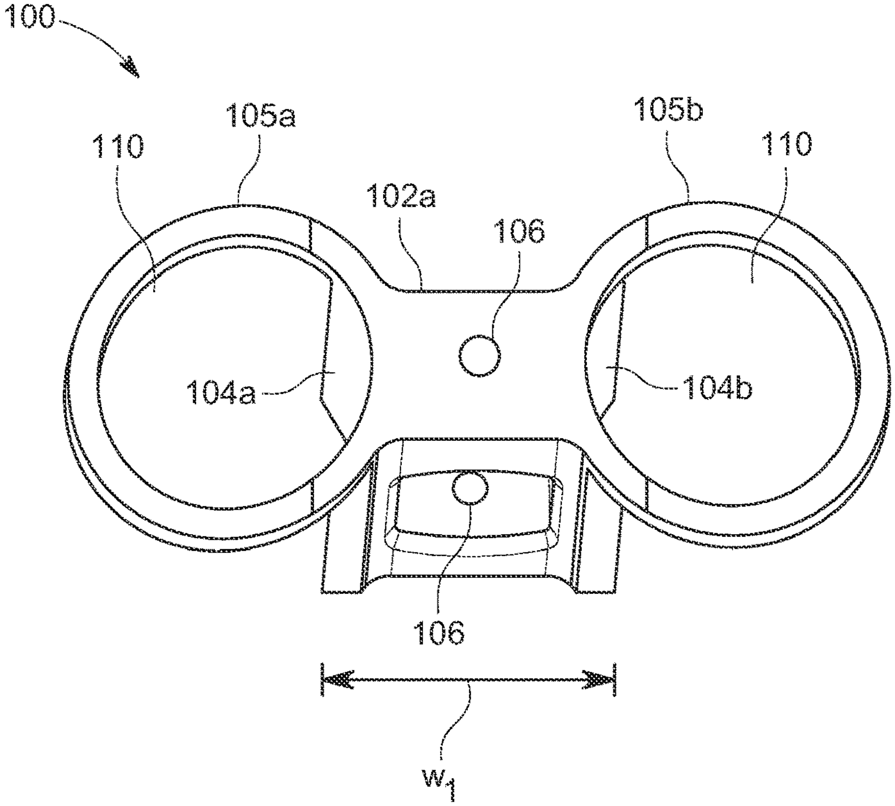

As illustrated in FIGS. 3E and 3F, in a preferred embodiment, the elongated member securing means comprises first and second open regions 105*a*, 105*b*, comprising openings 110 that are sized and configured to releasably receive and allow the first and second elongated members 176*a*, 176*b* to slidably translate therethrough.

In a preferred embodiment, the openings 110 in the first and second open regions 105*a*, 105*b* have a shape that substantially corresponds to the cross-sectional shape of the first and second elongated members 176*a*, 176*b*.

According to the invention, the elongated member securing means can comprise additional open regions to further stabilize the first and second elongated members 176*a*, 176*b*, when received by the elongated member securing means.

Figure 3G:
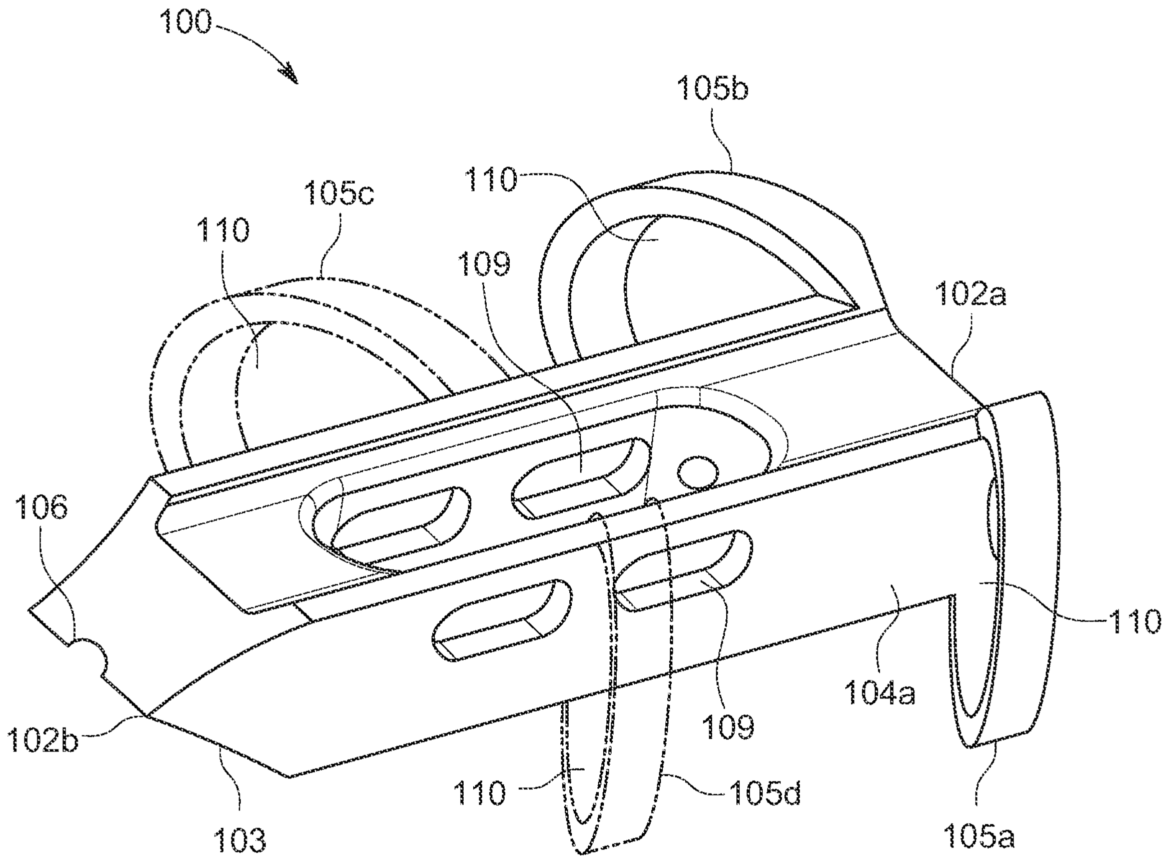

By way of example, in some embodiments, the elongated member securing means comprises third and fourth open regions 105*c*, 105*d*, as shown in phantom in FIG. 3G.

As further illustrated in FIGS. 3E and 3F, the central member 100 of the multi-member bone structure prosthesis 170 further comprises opposing first and second concave seat regions 104*a*, 104*b* that are configured to seat the first and second elongated members 176*a*, 176*b*, as illustrated in FIG. 3A.

As further illustrated in FIG. 3E, in a preferred embodiment, the distal end 102*b* of the central member 100 comprises a taper region 103, which is configured and adapted to disrupt, i.e., cut into and through, articular cartilage and cortical bone 8 (and, in some aspects, trabecular bone 10), which define a SI joint.

As illustrated in FIGS. 3A and 3F, in a preferred embodiment, the central member 100 of the multi-component prosthesis 170 further comprises a guidewire lumen 106 extending from the proximal end 102*a* to the distal end 102*b* of the central member 100, which is sized and configured to receive an elongated guide pin or wire, such as the elongated guide pin described in Co-pending U.S. application Ser. No. 17/833,960, therein.

As illustrated in FIGS. 3A-3D, in a preferred embodiment, the distal ends 179*b* of the first and second elongated members 176*a*, 176*b* also preferably comprise tapered regions 184*a*, 184*b*, respectively, which facilitate insertion of the distal ends 179*b* of the first and second elongated members 176*a*, 176*b* into pilot SI joint openings and, thereby dysfunctional SI joints.

According to the invention, the first and second elongated members 176*a*, 176*b* can comprise any suitable length to accommodate placement of the multi-member bone structure prosthesis 170 in various SI joints and other bone structures.

In some embodiments, the first and second elongated members 176*a*, 176*b* comprise a length less than 50 mm.

In some embodiments, the first and second elongated members 176*a*, 176*b* comprise a length in the range of 20-50 mm.

According to the invention, the first and second elongated members 176*a*, 176*b* can also comprise different or offset lengths. By way of example, the first elongated member 176*a* can thus comprise a length of 30 mm and the second elongated member 176*b* can comprise a length of 40 mm.

According to the invention, the first and second elongated members 176*a*, 176*b* can also comprise any suitable outer diameter (or cross-sectional area) to accommodate advancement of first and second elongated members 176*a*, 176*b* into various sizes of pilot SI joint openings.

Thus, in some embodiments, the first and second elongated members 176*a*, 176*b* comprise an outer diameter in the range of approximately 5.0-20.0 mm (or cross-sectional area in the range of ~19.63-314.16 $mm^2$).

According to the invention, the first and second elongated members 176*a*, 176*b* can comprise any suitable shape and configuration.

As illustrated in FIGS. 3A-3C, in some embodiments, the first and second elongated members 176*a*, 176*b* comprise a substantially cylindrical shape.

Figure 3H:
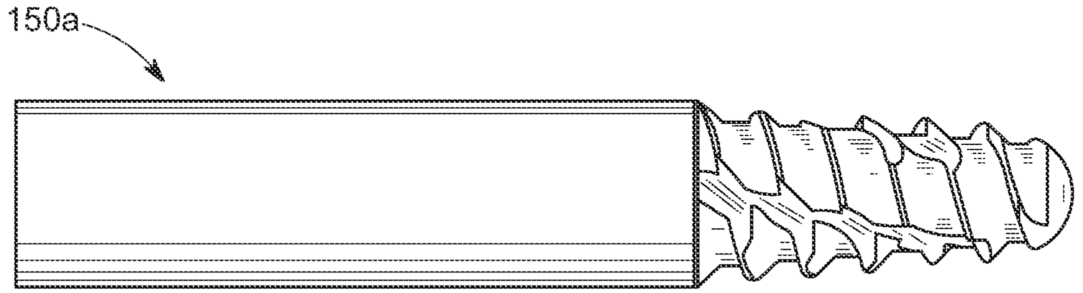
FIG. 3H is a side plan view of one embodiment of a threaded elongated member that can be employed with the multi-member prosthesis shown in FIG. 3A, in accordance with the invention.
Figure 3I:
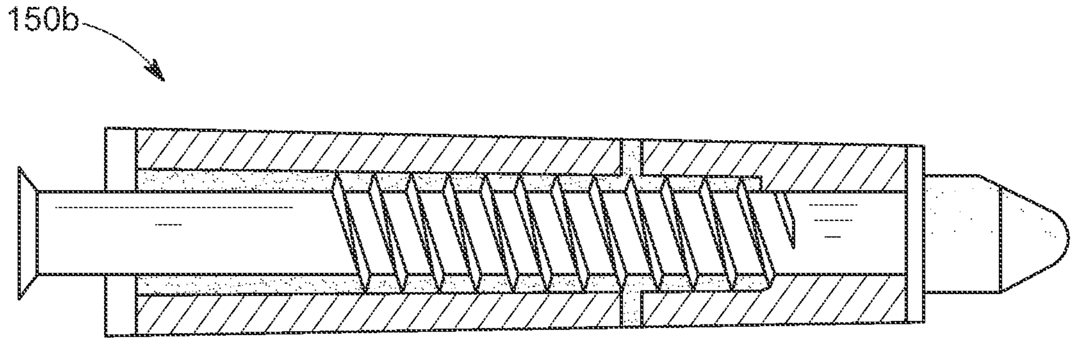
FIG. 3I is a side plan view of another embodiment of a threaded elongated member that can be employed with the multi-member prosthesis shown in FIG. 3A, in accordance with the invention.
Figure 3J:
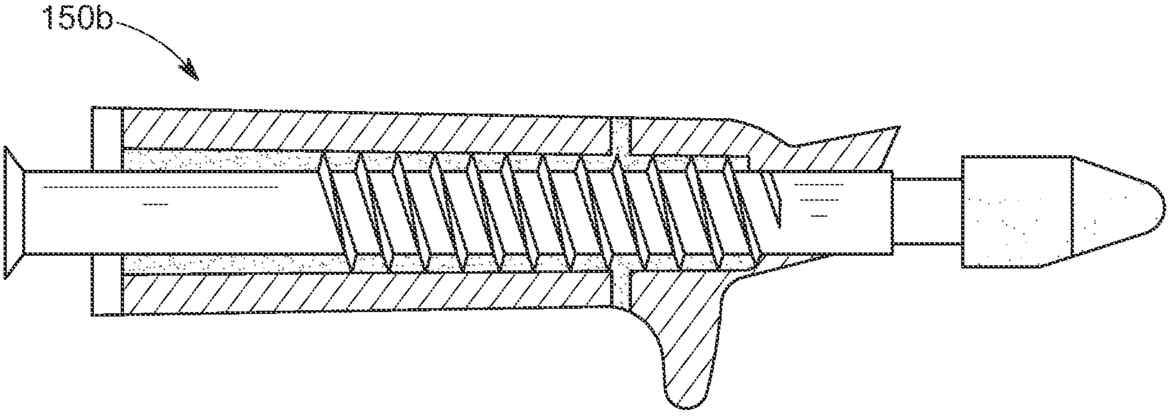
FIG. 3J is a side plan view of the threaded elongated member shown in FIG. 3I in a post-deployment configuration, in accordance with the invention.
Figure 3K:
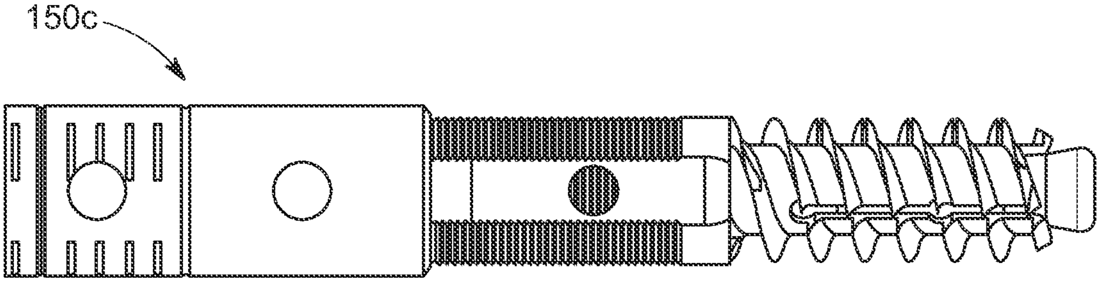
FIG. 3K is a side plan view of yet another embodiment of a threaded elongated member that can be employed with the multi-member prosthesis shown in FIG. 3A, in accordance with the invention.
Figure 3L:
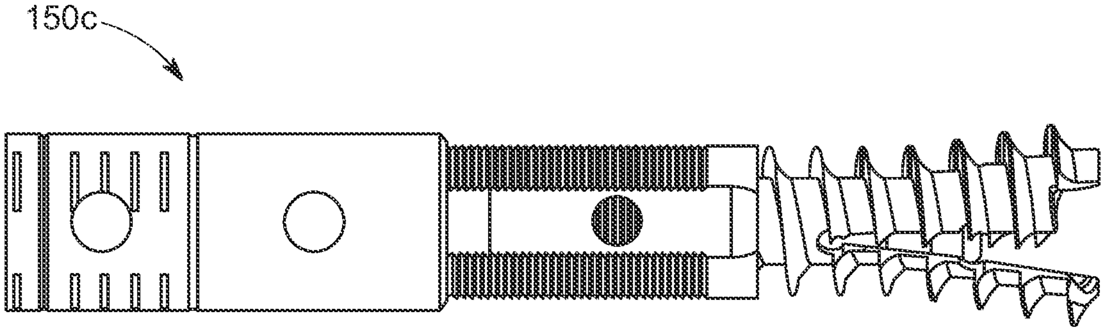
FIG. 3L is a side plan view of the threaded elongated member shown in FIG. 3K in a post-deployment configuration, in accordance with the invention.

According to the invention, the first and second elongated members 176*a*, 176*b* can also comprise threaded members and mechanisms. Exemplar threaded members and mechanisms include, without limitation, the threaded elongated member 150*a* illustrated in FIG. 3H, comprising a threaded distal end, the threaded elongated member 150*b* illustrated in FIGS. 3I and 3J, comprising a molly bolt mechanism; FIG. 3I illustrating the elongated member 150*b* in a pre-deployment configuration and FIG. 3J illustrating the elongated member 150*b* in a post-deployment configuration, and the threaded elongated member 150*c*, comprising an anchor bolt mechanism, illustrated in FIGS. 3K and 3L; FIG. 3K illustrating the elongated member 150*c* in a pre-deployment configuration and FIG. 3L illustrating the elongated member 150*c* in a post-deployment configuration, and like members and mechanisms.

A further exemplar molly bolt mechanism is disclosed in U.S. application Ser. No. 12/408,955, which is incorporated by reference herein, and a further exemplar anchor bolt mechanism is disclosed in U.S. Pat. No. 10,166,056, which is also incorporated by reference herein.

Figure 3M:
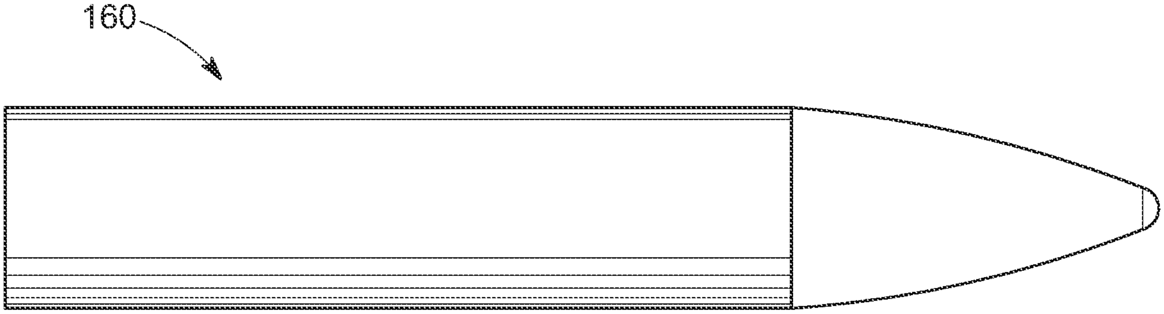
FIG. 3M is a side plan view of a non-threaded elongated member, i.e., pin, that can be employed with the multi-member prosthesis shown in FIG. 3A, in accordance with the invention.

The first and second elongated members 176*a*, 176*b* can also comprise a simple pin configuration, such as pin 160 shown in FIG. 3M.

According to the invention, the above referenced alternative elongated members can similarly comprise hollow, fenestrated structures, i.e., comprise apertures and/or slots and internal lumens; the internal lumens preferably adapted to receive and contain adhesive compositions and/or biologically active agent compositions and/or pharmacological agent compositions of the invention therein.

According to the invention, one or both of the first and second elongated members 176*a*, 176*b* can further comprise one of the bone stabilizing prostheses described in Applicant's Co-pending U.S. application Ser. No. 17/834,392, which is incorporated by reference herein in its entirety, and/or one of the multi-function bone structure prostheses described in Applicant's Co-pending U.S. application Ser. No. 17/903,310, which is also incorporated by reference herein in its entirety.

In some embodiments of the invention, to achieve sufficient engagement of the first and second elongated members 176*a*, 176*b* in a pilot SI joint opening, such as pilot SI joint opening 1000 illustrated in FIGS. 6A and 6B, and, thereby, a dysfunctional SI joint, preferably, the cross-sectional areas of the elongated members 176*a*, 176*b* are at least 0.05% greater than the cross-sectional areas defined by the sacrum and ilium portions of the pilot SI joint opening, e.g., sacrum and ilium portions 1003, 1004 of pilot SI joint opening 1000.

According to the invention, the central member 100 of the multi-member bone structure prosthesis 170 can similarly comprise any suitable length to accommodate placement of the prosthesis 170 in various SI joints and other bone structures.

In a preferred embodiment, the length of the central member 100 is at least 50%, more preferably, at least 70% of the length of the first and/or second elongated members 176*a*, 176*b*.

According to the invention, the central member 100 can also comprise any suitable width to accommodate placement of the central member 100 in various SI joints and other bone structures.

In some embodiments, the central member 100 comprises a width (denoted "$w_1$" in FIG. 3F) from the first concave seat region 104*a* to the second concave seat region 104*b* in the range of approximately 4.5-30 mm.

In a preferred embodiment, when the first and second elongated members 176*a*, 176*b* of the multi-member bone structure prosthesis 170 are secured to the central member 100 and the multi-member bone structure prosthesis 170 is disposed in a SI joint, as described above, the multi-member bone structure prosthesis 170 is transfixed thereto, i.e., the first elongated member 176*a* is transfixed to the ilium bone structure, the second elongated member 176*b* is transfixed to the sacrum bone structure (or vice versa), and the central member 100 is transfixed to the interface between the ilium and sacrum bone structures.

Referring now to FIGS. 4A-4G, there are shown depictions of another embodiment of a multi-member bone structure prosthesis (denoted "270") of the invention.

Figure 4A:
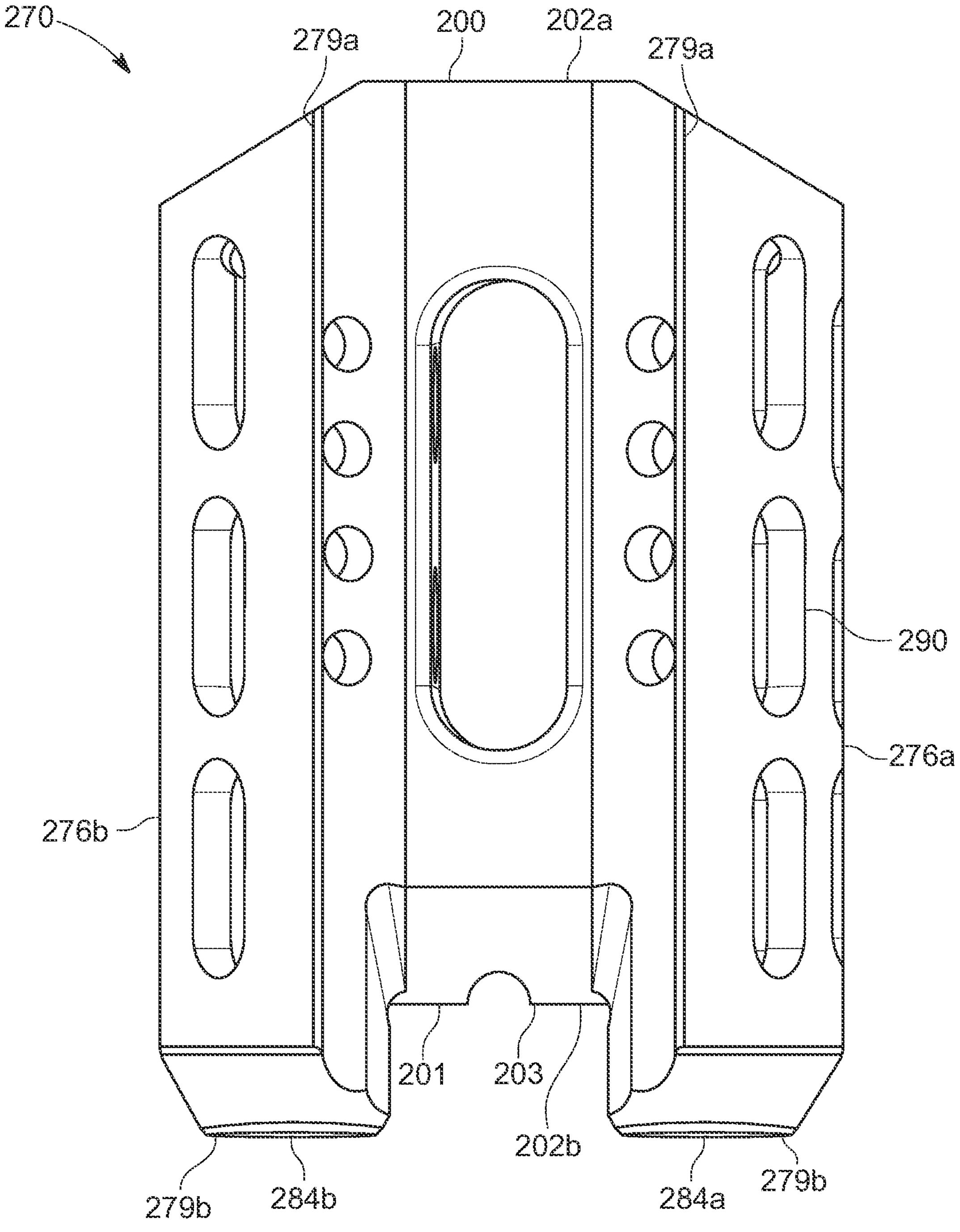
FIG. 4A is a front plan view of another embodiment of a multi-member bone structure prosthesis, in accordance with the invention.

As illustrated in FIG. 4A, the multi-member bone structure prosthesis 270 (also similarly referred to hereinafter as a "multi-member prosthesis"), comprises a biocompatible and, hence, implantable member comprising first and second elongated members 276*a*, 276*b* and a central member 200; the first and second elongated members 276*a*, 276*b* comprising proximal and distal ends 279*a*, 279*b* and the central member 200 comprising proximal and distal ends 202*a*, 202*b*.

In a preferred embodiment, the first elongated member 276*a* preferably comprises a cross-sectional shape that corresponds to at least a portion of the cross-sectional shape of a first portion of a pilot SI joint opening in the dysfunctional SI joint, such as the sacrum portion 1003 of the pilot SI joint opening 1000 shown in FIGS. 6A and 6B, and the second elongated member 276*b* similarly preferably comprises a cross-sectional shape that corresponds to at least a portion of the cross-sectional shape of a second portion of the pilot SI joint opening in the dysfunctional SI joint, such as the ilium portion 1004 of the pilot SI joint opening 1000.

Figure 4B:
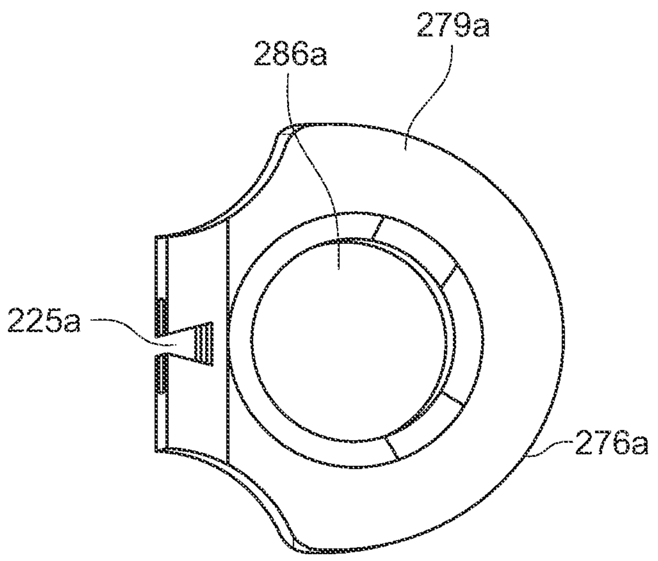
FIG. 4B is a top plan view of the right-side elongated member of the multi-member prosthesis shown in FIG. 4A, in accordance with the invention.
Figure 4C:
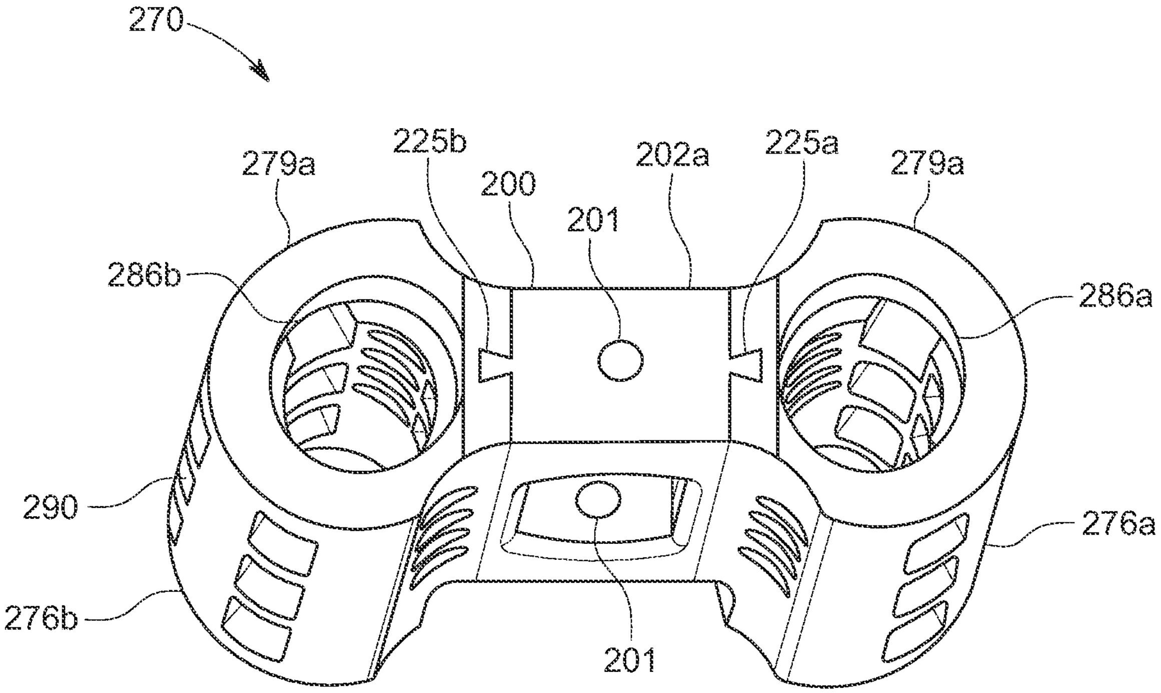
FIG. 4C is a top perspective view of the multi-member prosthesis shown in FIG. 4A, in accordance with the invention.

As illustrated in FIGS. 4B and 4C, in a preferred embodiment, the first and second elongated members 276*a*, 276*b* comprise rail slots or seats 225*a*, 225*b* that are sized and configured to receive the elongated member rails 224*a*, 224*b* of the central member 200 discussed below.

As illustrated in FIG. 4C, the first elongated member 276*a* further comprises a first elongated member internal lumen 286*a* and the second elongated member 276*b* further comprises a second elongated member internal lumen 286*b*.

In a preferred embodiment, the distal ends 279*b* of the first and second elongated members 276*a*, 276*b* similarly comprise closed distal ends, whereby the first and second elongated member internal lumens 286*a*, 286*b* do not extend through the distal ends 279*b* of the first and second elongated members 276*a*, 276*b*.

In a preferred embodiment, the first and second elongated member internal lumens 286*a*, 286*b* are similarly configured to receive agents and compositions that facilitate adhesion of the first and second elongated members 276*a*, 276*b* and, hence, multi-member bone structure prosthesis 270 to and, hence, in dysfunctional SI joints.

In a preferred embodiment, the first and second elongated member internal lumens 286*a*, 286*b* are also similarly configured to receive one or more the aforementioned biologically active agents and compositions, including osteogenic agents and compositions, and pharmacological agents and compositions that promote or induce proliferation, and/or growth and/or remodeling and/or regeneration of osseous tissue and/or facilitate osseous tissue ingrowth into the multi-member bone structure prosthesis 270 when the prosthesis 270 is disposed in a dysfunctional SI joint.

Figure 4D:
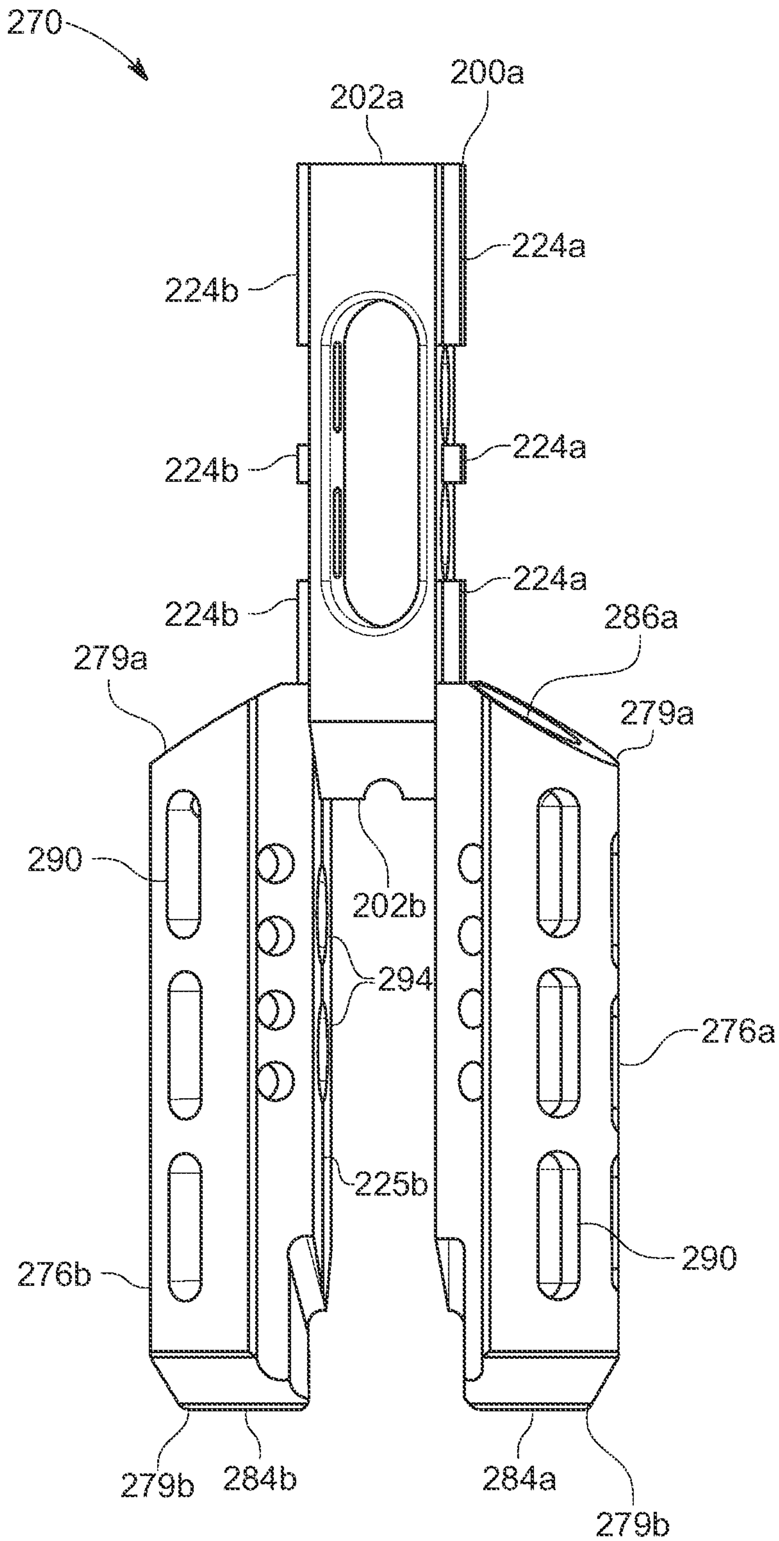
FIG. 4D is a further front plan view of the multi-member prosthesis shown in FIG. 4A illustrating the elongated members partially engaged to the central member, in accordance with the invention.
Figure 4E:
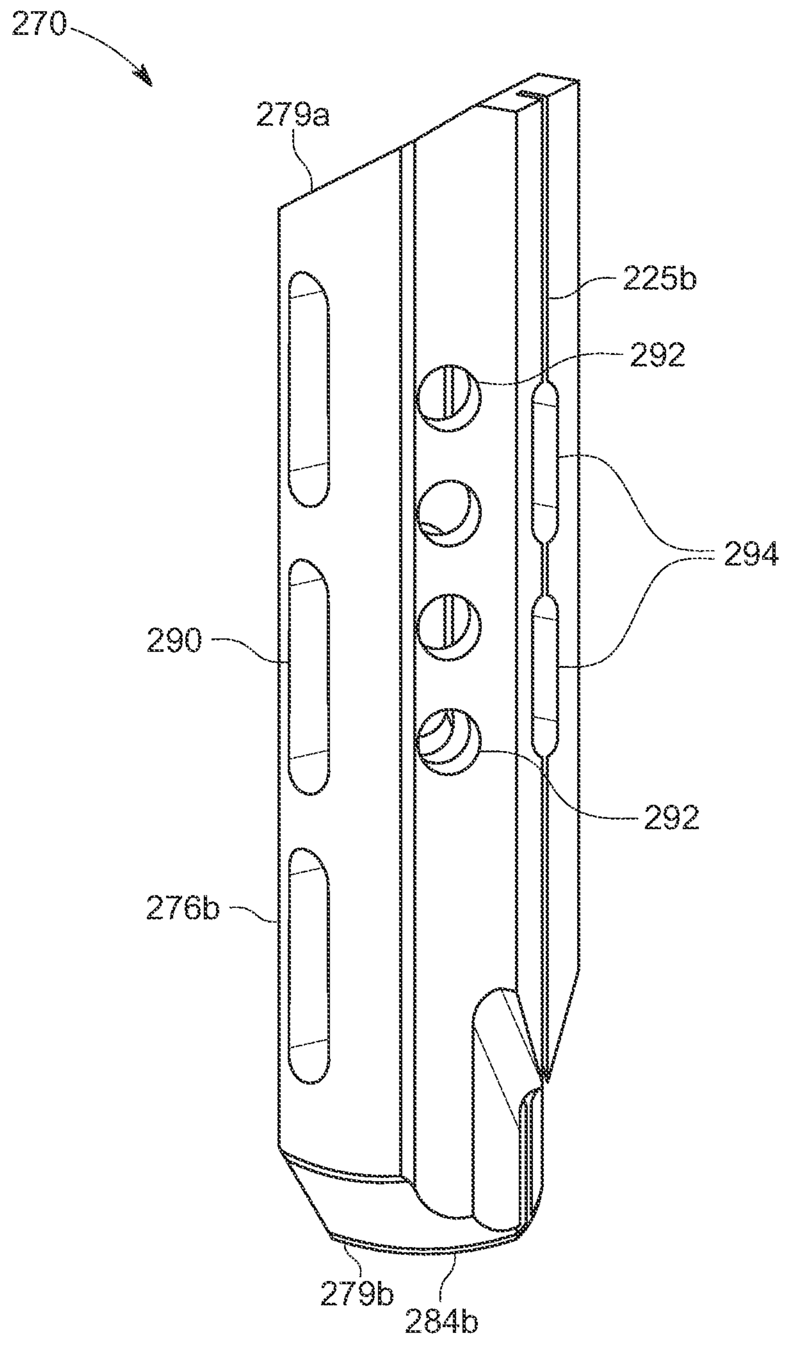
FIG. 4E is a perspective view of the left-side elongated member of the multi-member prosthesis shown in FIG. 4A, in accordance with the invention.

As further illustrated in FIGS. 4A, 4D and 4E, in a preferred embodiment, the first and second elongated members 276*a*, 276*b* further comprise a plurality of slots 290, 294 and apertures 292, which preferably are similarly in communication with the first and second elongated member internal lumens 286*a*, 286*b*; the first and second elongated members 276*a*, 276*b* thus similarly comprising hollow, fenestrated members.

In a preferred embodiment, the slots 290, 294 and apertures 292 are similarly sized and configured to allow the adhesive compositions and/or biologically active agent compositions and/or pharmacological agent compositions to be dispersed out of the first and second elongated member internal lumens 286*a*, 286*b* and delivered to a dysfunctional SI joint when the multi-component prosthesis 270 is disposed therein.

In a preferred embodiment, when the first and second elongated members 276*a*, 276*b* of the multi-member bone structure prosthesis 270 are slidably received by the central member 200, as illustrated in FIG. 4A and discussed below, slots 294 are similarly preferably aligned with slots 209 of the central member 200 to facilitate osseous tissue ingrowth into the multi-member prosthesis 270 when the prosthesis 270 is disposed in a dysfunctional SI joint.

In some embodiments of the invention, the first and second elongated member internal lumens 286*a*, 286*b* also comprise internal threads proximate the proximal ends 279*a* thereof, such as the internal prosthesis engagement member lumens 86*a*, 86*b* of the single-member bone structure prosthesis 70 shown in FIGS. 2E and 2F, to cooperate with a prosthesis deployment instrument that is adapted to advance the first and second elongated members 276*a*, 276*b* to and into a bone structure; particularly, a dysfunctional SI joint.

In a preferred embodiment, the central member 200 similarly comprises elongated member securing means sized and configured to releasably receive and secure the first and second elongated members 276*a*, 276*b* to the central member 200, as illustrated in FIG. 4A.

Figure 4F:
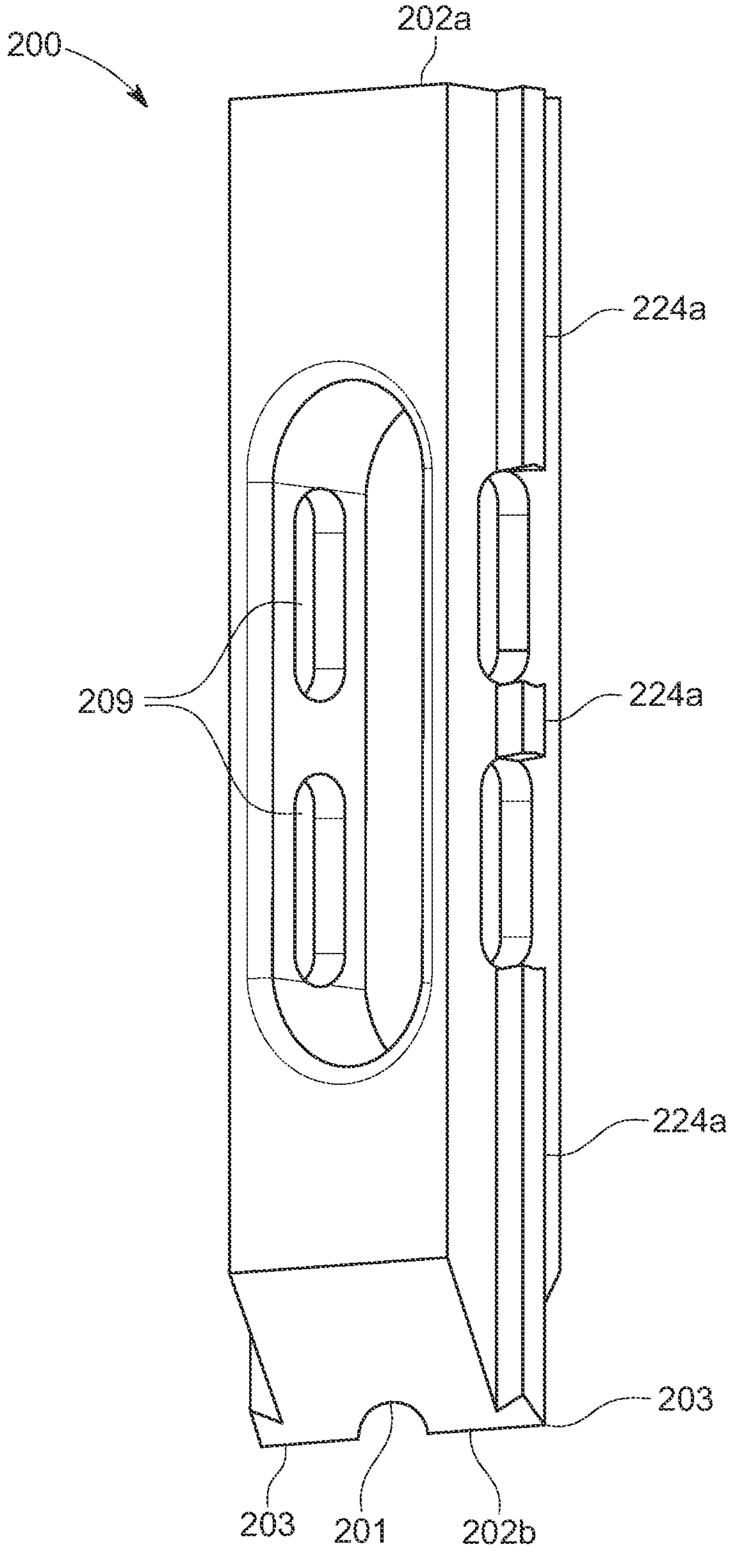
FIGS. 4F and 4G are perspective views of the central member of the multi-member prosthesis shown in FIG. 4A, in accordance with the invention.
Figure 4G:
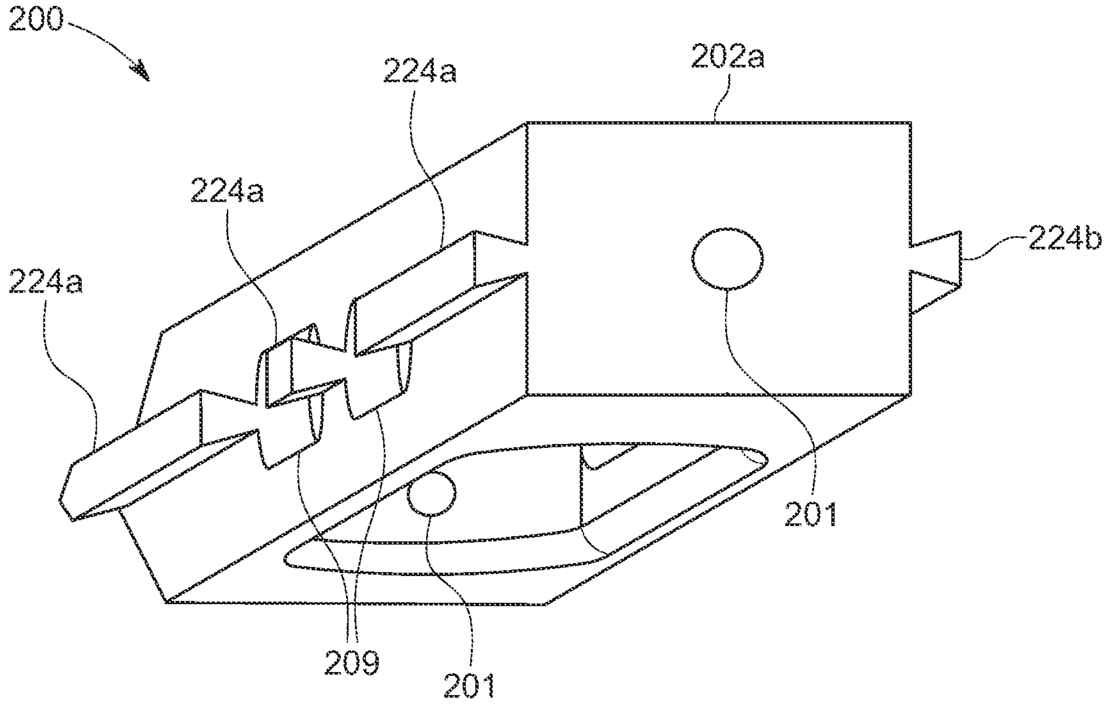

As illustrated in FIGS. 4C and 4G, in a preferred embodiment, the elongated member securing means comprises first and second discontinuous rails 224*a*, 224*b* that are sized and configured to be received in the rail slots or seats 225*a*, 225*b* of the first and second elongated members 276*a*, 276*b* (discussed below), whereby the first and second elongated members 276*a*, 276*b* are secured to the central member 200.

According to the invention, the first and second discontinuous rails 224*a*, 224*b* and rail slots 225*a*, 225*b* can comprises various corresponding shapes, e.g., square, triangular, round, etc., and sizes.

As illustrated in FIGS. 4C and 4G, in one embodiment, the first and second discontinuous rails 224*a*, 224*b* and rail slots 225*a*, 225*b* comprise corresponding substantially triangular shapes.

As further illustrated in FIG. 4F, in a preferred embodiment, the distal end 202*b* of the central member 200 similarly comprises a taper region 203, which is configured and adapted to disrupt, i.e., cut into and through, articular cartilage and cortical bone 8 (and, in some aspects, trabecular bone 10), which define a SI joint.

As illustrated in FIGS. 4C and 4G, in a preferred embodiment, the central member 200 of the multi-component prosthesis 270 further comprises a guidewire lumen 201 extending from the proximal end 202*a* to the distal end 202*b* of the central member 200, which is similarly sized and configured to receive an elongated guide pin or wire, such as the elongated guide pin described in Co-pending U.S. application Ser. No. 17/833,960, therein.

As illustrated in FIGS. 4A, 4D and 4E, in a preferred embodiment, the distal ends 279*b* of the first and second elongated members 276*a*, 276*b* also preferably comprise tapered regions 284*a*, 284*b*, respectively, which facilitate insertion of the distal ends 279*b* of the first and second elongated members 276*a*, 276*b* into pilot SI joint openings and, thereby dysfunctional SI joints.

According to the invention, the first and second elongated members 276*a*, 276*b* can similarly comprise any suitable length to accommodate placement of the multi-member bone structure prosthesis 270 in various SI joints and other bone structures.

In some embodiments, the first and second elongated members 276*a*, 276*b* similarly comprise a length less than 50 mm.

In some embodiments, the first and second elongated members 276*a*, 276*b* comprise a length in the range of 20-50 mm.

According to the invention, the first and second elongated members 276*a*, 276*b* can also similarly comprise different or offset lengths. Again, by way of example, the first elongated member 276*a* can thus comprise a length of 30 mm and the second elongated member 276*b* can comprise a length of 40 mm.

According to the invention, the first and second elongated members 276*a*, 276*b* can also comprise any suitable outer diameter (or cross-sectional area) to accommodate advancement of first and second elongated members 276*a*, 276*b* into various sizes of pilot SI joint openings.

Thus, in some embodiments, the first and second elongated members **276*a*, 276*b*** comprise a cross-sectional area in the range of ~19.63-314.16 mm$^2$.

According to the invention, the first and second elongated members **276*a*, 276*b*** can similarly comprise any suitable shape and configuration.

As illustrated in FIGS. 4B and 4C, in some embodiments, the first and second elongated members **276*a*, 276*b*** comprise a partially cylindrical shape.

According to the invention, the first and second elongated members **276*a*, 276*b* can also similarly comprise the threaded members and mechanisms illustrated in FIGS. 3H-3L, and the pin configuration and structure illustrated in FIG. 3**M, and like structures.

According to the invention, the above referenced alternative elongated members can similarly comprise hollow, fenestrated structures, i.e., comprise apertures and/or slots and internal lumens; the internal lumens preferably adapted to receive and contain adhesive compositions and/or biologically active agent compositions and/or pharmacological agent compositions of the invention therein.

According to the invention, one or both of the first and second elongated members **276*a*, 276*b*** can similarly additionally comprise one of the bone stabilizing prostheses described in Applicant's Co-pending U.S. application Ser. No. 17/834,392 and/or one of the multi-function bone structure prostheses described in Applicant's Co-pending U.S. application Ser. No. 17/903,310.

According to the invention, the aforementioned threaded members and mechanisms, bone stabilizing prostheses, and multi-function bone structure prostheses can also comprise at least one rail slot or seat that is sized and configured to receive the first and second discontinuous rails **224*a*, 224*b* of the central member 200**.

In some embodiments of the invention, to achieve sufficient engagement of the first and second elongated members **276*a*, 276*b* in a pilot SI joint opening, such as pilot SI joint opening 1000 illustrated in FIGS. 6A and 6B, and, thereby, a dysfunctional SI joint, preferably, the cross-sectional areas of the elongated members 276*a*, 276*b* are similarly at least 0.05% greater than the cross-sectional areas defined by the sacrum and ilium portions of the pilot SI joint opening, e.g., sacrum and ilium portions 1003, 1004 of pilot SI joint opening 1000**.

According to the invention, the central member 200 of the multi-member bone structure prosthesis 270 can similarly comprise any suitable length to accommodate placement of the prosthesis 270 in various SI joints and other bone structures.

In a preferred embodiment, the length of the central member 200 is similarly at least 50%, more preferably, at least 70% of the length of the first and/or second elongated members **276*a*, 276*b***.

According to the invention, the central member 200 can also similarly comprise any suitable width to accommodate placement of the central member 200 in various SI joints and other bone structures. In some embodiments, the central member 200 similarly comprises a width in the range of approximately 4.5-30 mm.

In a preferred embodiment, when the first and second elongated members **276*a*, 276*b* of the multi-member bone structure prosthesis 270 are secured to the central member 200 and the multi-member bone structure prosthesis 270 is disposed in a SI joint, as described above, the multi-member bone structure prosthesis 270 is similarly transfixed thereto, i.e., the first elongated member 276*a* is transfixed to the ilium bone structure, the second elongated member 276*b* is transfixed to the sacrum bone structure (or vice versa), and the central member 200** is transfixed to the interface between the ilium and sacrum bone structures.

Figure 5A:
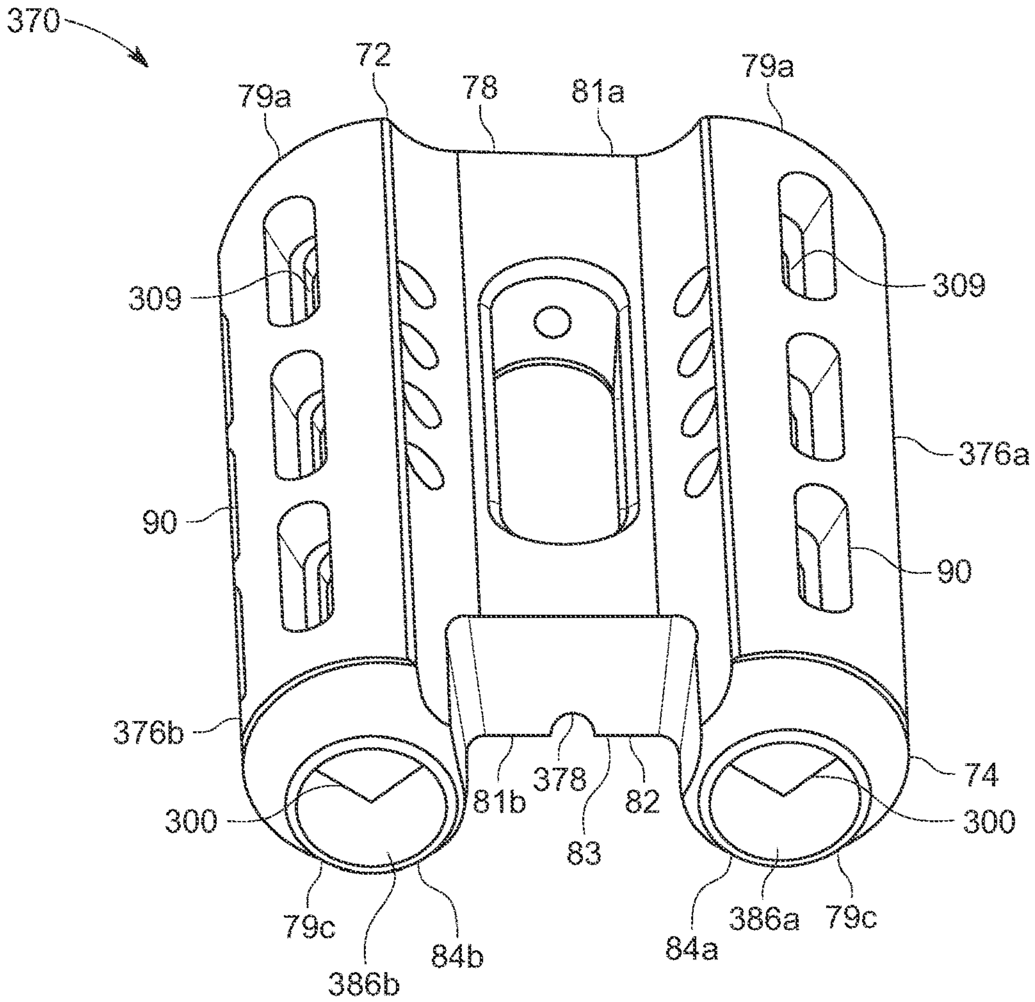
FIG. 5A is a front perspective view of another embodiment of a multi-member bone structure prosthesis, in accordance with the invention.

Referring now to FIG. 5A, there is shown a depiction of a further embodiment of the multi-member bone structure prosthesis (denoted "370").

As illustrated in FIG. 5A, the multi-member bone structure prosthesis comprises the same basic structure and, hence, features of the single-member bone structure prosthesis 70 illustrated in FIGS. 2A-2F and discussed in detail above.

However, as further illustrated in FIG. 5A, the first and second prosthesis or pontoon sections (now denoted "**376*a*" and "376*b*") comprise open distal ends 79*c*, i.e., the internal lumens (now denoted "386*a*" and "386*b***") extend therethrough.

Figure 5B:
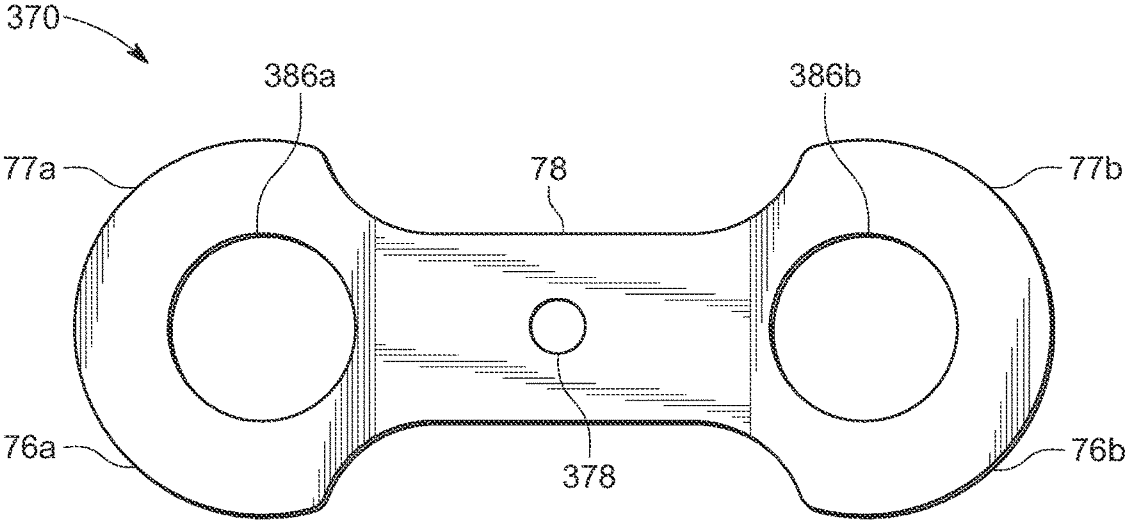
FIG. 5B is a top plan view of the multi-member prosthesis shown in FIG. 5A, in accordance with the invention.

As illustrated in FIGS. 5A and 5B, in some embodiments, the bridge section 78 also similarly comprises an internal lumen 378 that extends from the proximal end **81*a* to the distal end 81*b*** that is sized and configured to receive an elongated guide pin or wire, such as the elongated guide pin described in Co-pending U.S. application Ser. No. 17/833,960.

As further illustrated in FIG. 5A, in this embodiment, each continuous internal prosthesis engagement member lumen **386*a*, 386*b* is further sized and configured to receive a bone structure engagement member 300 of the invention, and, preferably, allow the bone structure engagement member 300** to slidably translate therethrough.

Figure 5D:
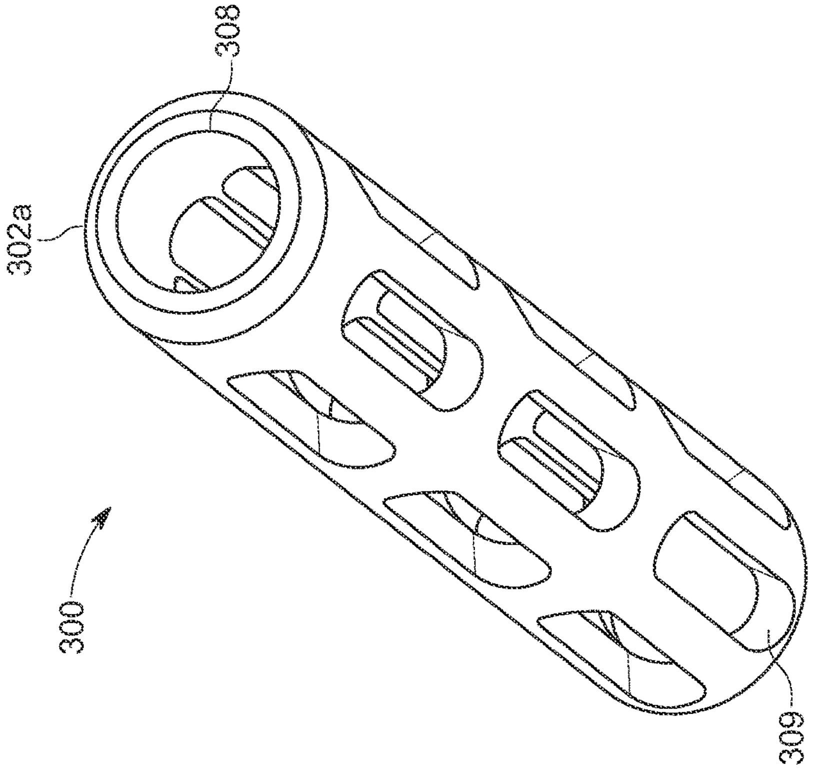
FIGS. 5D and 5E are perspective views of the bone structure engagement member shown in FIG. 5C, in accordance with the invention.
Figure 5C:
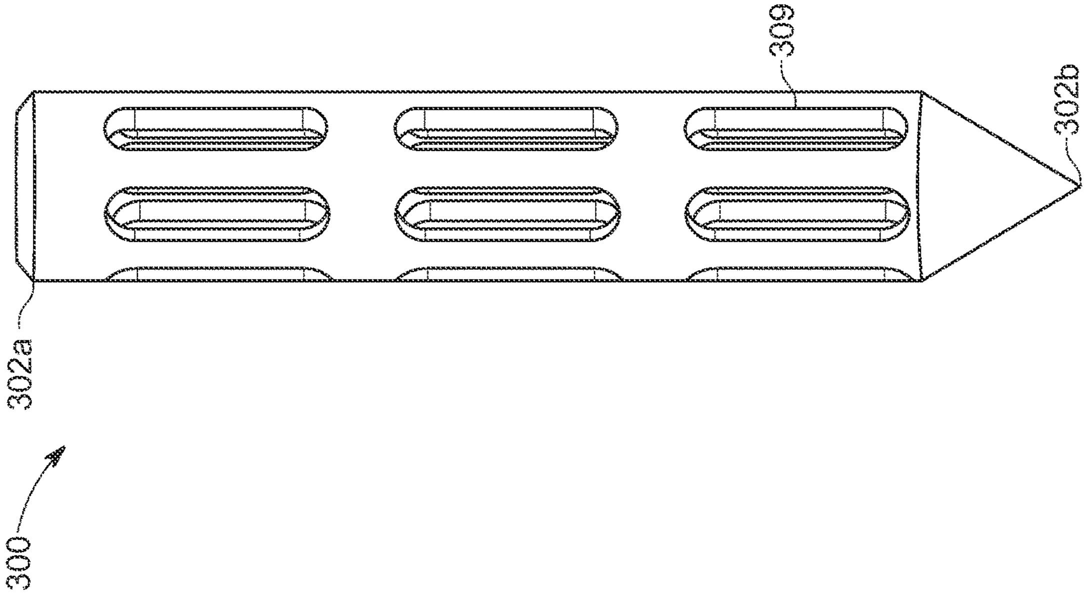
FIG. 5C is a front plan view of a bone structure engagement member or rod, in accordance with the invention.
Figure 5E:
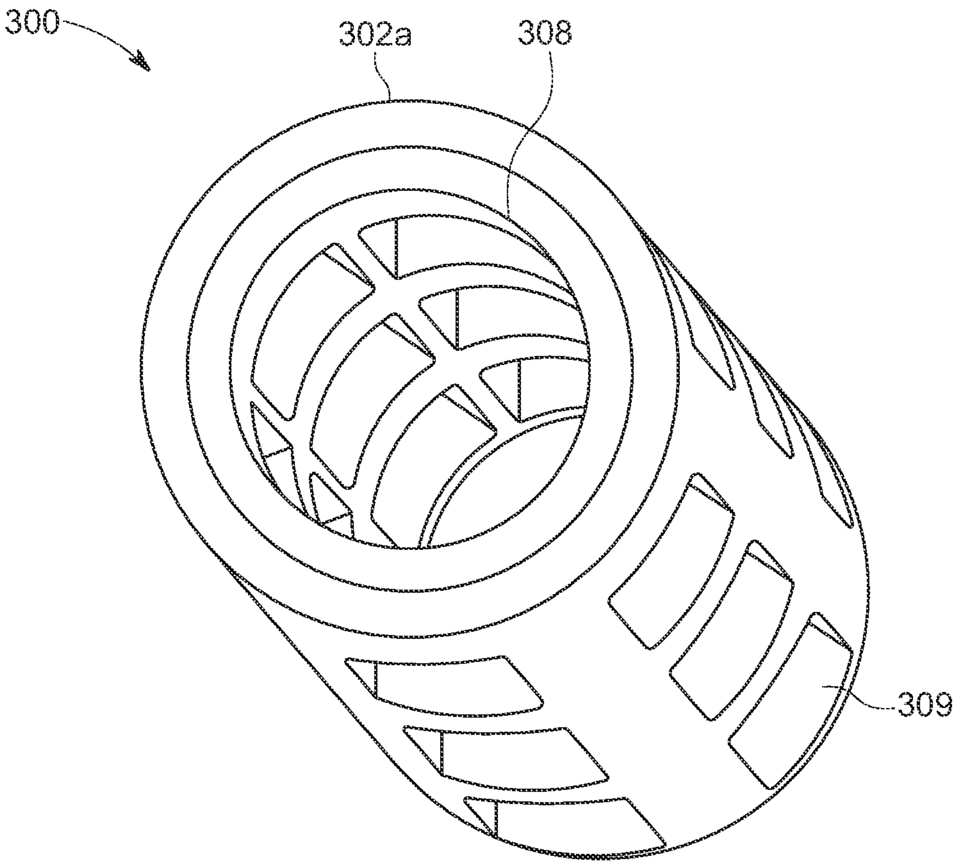

As illustrated in FIGS. 5C-5E, the bone structure engagement member 300 comprises proximal and distal ends **302*a*, 302*b*; the distal end 302*b* comprising a closed pointed end that facilitates advancement of the member 300** into pilot SI joint openings and directly into bone structures.

As illustrated in FIGS. 5D and 5E, the bone structure engagement member 300 further comprises an internal lumen 308 and a plurality of slots 309 that are in communication with the internal lumen 308.

In a preferred embodiment, the slots 309 comprise a similar shape of the slots 90 in the first and second prosthesis sections **376*a*, 376*b***.

As further illustrated in FIG. 5A, in a preferred embodiment, when the bone structure engagement members 300 are slidably received and positioned in the internal lumens **386*a*, 386*b* of the first and second prosthesis sections 376*a*, 376*b*, slots 309 and slots 90 are substantially aligned, whereby, when an adhesive composition and/or biologically active agent composition and/or pharmacological agent composition is disposed in the internal lumens 386*a*, 386*b*, the slots 390 and 90 allow the adhesive composition and/or biologically active agent composition and/or pharmacological agent composition to be dispersed out of the internal lumens 386*a*, 386*b* and delivered to a dysfunctional SI joint when the multi-component prosthesis 370** is disposed therein.

In some embodiments of the invention, the open distal ends **79*c* of the first and second elongated prosthesis sections 376*a*, 376*b* preferably comprise a smaller diameter than the bone structure engagement member 300 to abate movement, i.e., linear and rotational translation, of the bone structure engagement member 300 in the internal lumens 386*a*, 386*b***.

According to the invention, the bone structure engagement members 300 can comprise any suitable length. In some embodiments, the bone structure engagement members 300 comprise a length in the range of 20-50 mm.

According to the invention, the bone structure engagement members 300 can similarly comprise any suitable shape and configuration.

As illustrated in FIGS. 5C-5E, in some embodiments, the bone structure engagement members 300 comprise a substantially cylindrical shape.

According to the invention, the bone structure engagement members 300 can also similarly comprise threaded members and mechanisms similar to the threaded members and mechanisms illustrated in FIGS. 3H-3L, and like structures.

According to the invention, one or both of the bone structure engagement members 300 can similarly additionally comprise a structure similar to the bone stabilizing prostheses described in Applicant's Co-pending U.S. application Ser. No. 17/834,392 and/or the multi-function bone structure prostheses described in Applicant's Co-pending U.S. application Ser. No. 17/903,310.

In a preferred embodiment, when the multi-member bone structure prosthesis 370 is disposed in a SI joint, the multi-member bone structure prosthesis 370 is similarly transfixed thereto, i.e., the first prosthesis section 376*a* and a first bone structure engagement member 300 are transfixed to the ilium bone structure, the second prosthesis section 376*b* and a second bone structure engagement member 300 are transfixed to the sacrum bone structure (or vice versa), and the bridge section 78 is transfixed to the interface between the ilium and sacrum bone structures.

According to the invention, the single-member bone structure prosthesis 70 and multi-member bone structure prostheses 170, 270 and 370 and, hence members and components thereof, can comprise various biocompatible materials, including metals and metal alloys, such as titanium, stainless-steel, cobalt-chromium alloys and nickel-titanium alloys, and various biocompatible polymers, including, without limitation, reinforced polymers, such as carbon fiber reinforced polymers and metal-framed polymers.

The single-member bone structure prosthesis 70 and multi-member bone structure prostheses 170, 270 and 370 and, hence members and components thereof, can additionally comprise a porous structure to facilitate (i) bone or osseous tissue ingrowth into the single-member prosthesis 70 and multi-member prostheses 170, 270 and 370 and (ii) adhesion of the single-member prosthesis 70 and multi-member prostheses 170, 270 and 370 in a SI joint opening and, thereby, dysfunctional SI joint.

According to the invention, the single-member bone structure prosthesis 70 and multi-member bone structure prostheses 170, 270 and 370 and, hence members and components thereof, can further comprises an outer coating.

In some embodiments, the outer coating comprises one of the aforementioned osteogenic compositions.

In some embodiments, the osteogenic composition comprises a demineralized bone matrix, autograft bone material, allograft bone material, xenograft bone material, polymethyl-methacrylate or calcium-based bone material.

In some embodiments, the osteogenic composition comprises a bone morphogenic protein (BMP).

In some embodiments, the BMP comprises BMP-1, BMP2a, BMP2b, BMP3, BMP4, BMP5, BMP6, BMP7, or BMP8a.

In some embodiments, the outer coating comprises one of the aforementioned biologically active agents.

In some embodiments, the outer coating comprises one of the aforementioned pharmacological agents.

In some embodiments, the pharmacological agent comprises penicillin, a carboxypenicillin, a tetracycline, gentamicin, vancomycin, ciprofloxacin, amikacin, an aminoglycoside, a cephalosporin, clindamycin, erythromycin, a fluoroquinolone, a macrolide, an azolide, metronidazole, trimethoprim-sulfamethoxazole, polymyxin B, oxytetracycline, tobramycin, cefazolin, or rifampin.

In some embodiments of the invention, the outer coating comprises a biocompatible adhesive composition. Suitable adhesive compositions are set forth in priority U.S. application Ser. No. 17/833,960, which is incorporated by reference herein.

In some embodiments, the outer coating comprises one of the aforementioned polymers and/or compositions comprising same.

In some embodiments of the invention, the polymer comprises poly(glycerol sebacate) (PGS) or a derivative thereof, including, without limitation, poly(glycerol-co-sebacate) acrylate (PGSA) and PGS co-polymers, such as poly(glycerol sebacate)-co-poly(ethylene glycol) (PGS-PEG); and/or composites thereof, e.g., PGS-hydroxyapatite (HA) composites and PGS-poly(ε-caprolactone) (PGS-PCL) composites, and compositions comprising same.

As set forth in Applicant's Co-Pending U.S. application Ser. Nos. 17/469,132, 17/468,811, 17/463,831, and 17/834,392, PGS and derivatives thereof possess a unique property of inducing remodeling of damaged osseous or bone tissue and, hence, healing of the associated bone structures when disposed proximate thereto.

A further seminal property of PGS is that its physical state can be modulated during synthesis by controlling the "degree of esterification" via at least one crosslinking agent, e.g., methylene diphenyl diisocyanate (MDI), whereby the PGS exhibits adhesive properties.

As further set forth in Co-pending U.S. application Ser. Nos. 17/469,132, 17/468,811, 17/463,831 and 17/834,392, which are incorporated by reference herein, PGS and its derivatives; particularly, PGSA are also excellent platforms for delivery and, hence, administration of biologically active agents and pharmacological agents to mammalian tissue, including osseous or bone tissue.

Thus, in some embodiments of the invention, the PGS outer coatings and PGS and PGSA based compositions further comprise one or more of the aforementioned biologically active or pharmacological agents.

In some embodiments, the outer coating comprises a nickel-titanium alloy coating, such as the nickel-titanium alloy (i.e., Nitinol™) coatings disclosed in U.S. Pat. Nos. 9,278,000 and 9,750,850, which are incorporated by reference herein.

Although the single-member bone structure prosthesis 70 and multi-member bone structure prostheses 170, 270 and 370 are described in connection with stabilizing and, hence, treating a dysfunctional SI joint, according to the invention, the single-member bone structure prosthesis 70 and multi-member bone structure prostheses 170, 270 and 370 can also be employed to stabilize other articulating and non-articulating bone structures, including individual skeletal members.

As indicated above, the single-member bone structure prosthesis 70 and multi-member bone structure prostheses 170, 270 and 370 are configured and adapted to be advanced into pilot SI joint openings, such as pilot SI joint opening 1000 illustrated in FIGS. 6A and 6B, and, thereby, a dysfunctional SI joint.

According to the invention, the pilot SI joint openings can be created by various systems and means.

In some embodiments, the pilot SI joint openings are created by a drill guide assembly described in priority U.S. application Ser. No. 17/833,960.

In a preferred embodiment, the pilot SI joint openings are created by the drill guide assembly illustrated in FIGS. 7A-7F and discussed in detail below.

Figure 7A:
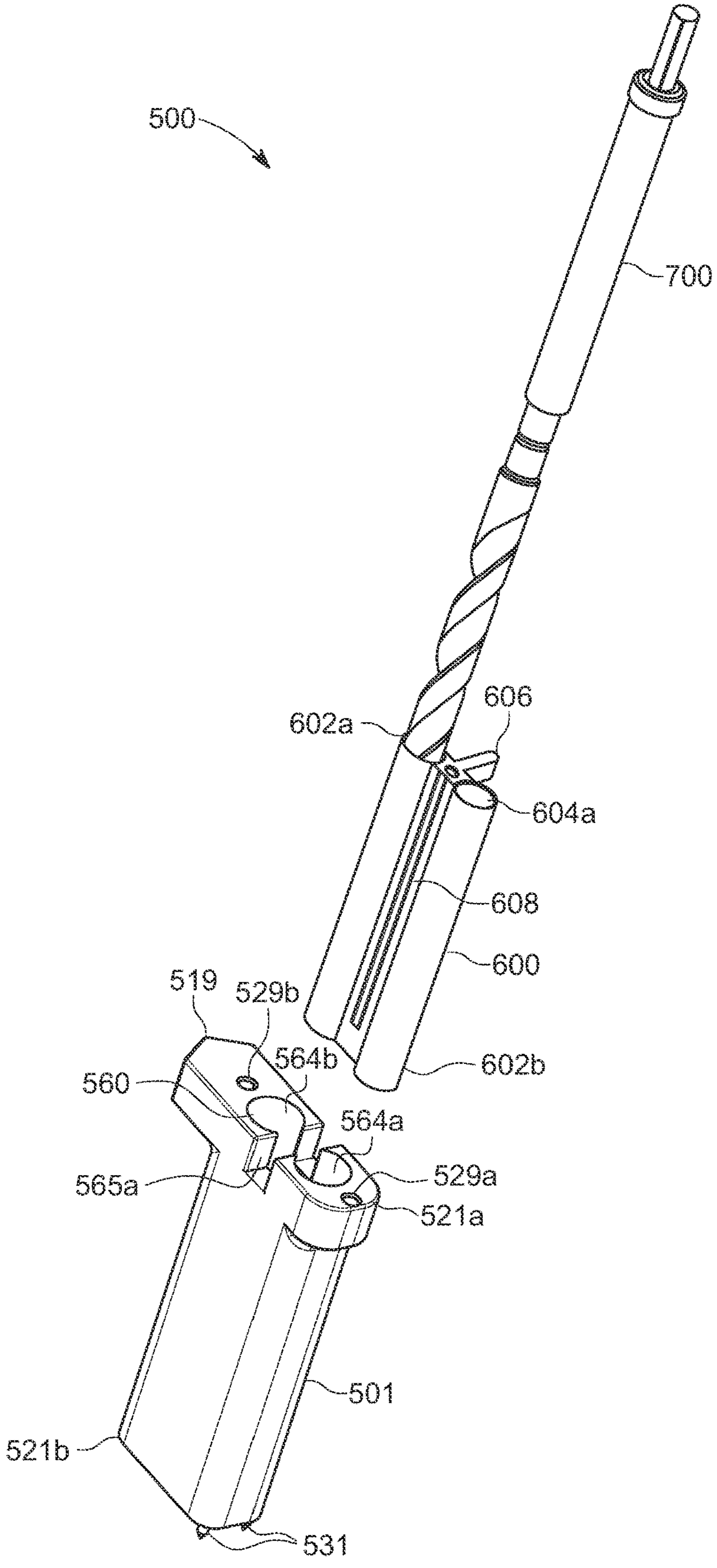
FIG. 7A is an exploded perspective view of a drill guide, in accordance with the invention.
Figure 7B:
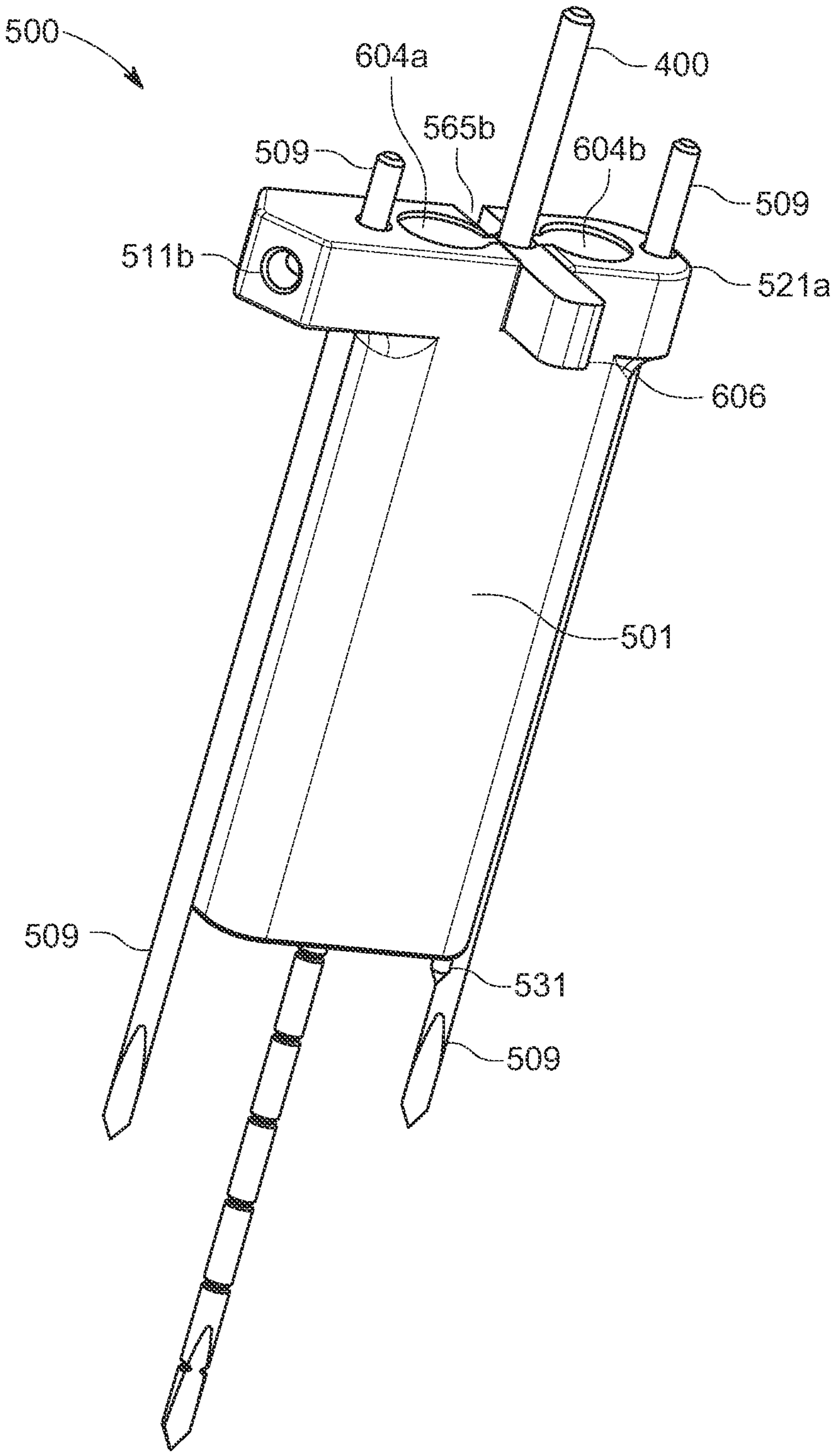
FIG. 7B is further perspective view of the drill guide shown in FIG. 7A in an assembled configuration, in accordance with the invention.
Figure 7D:
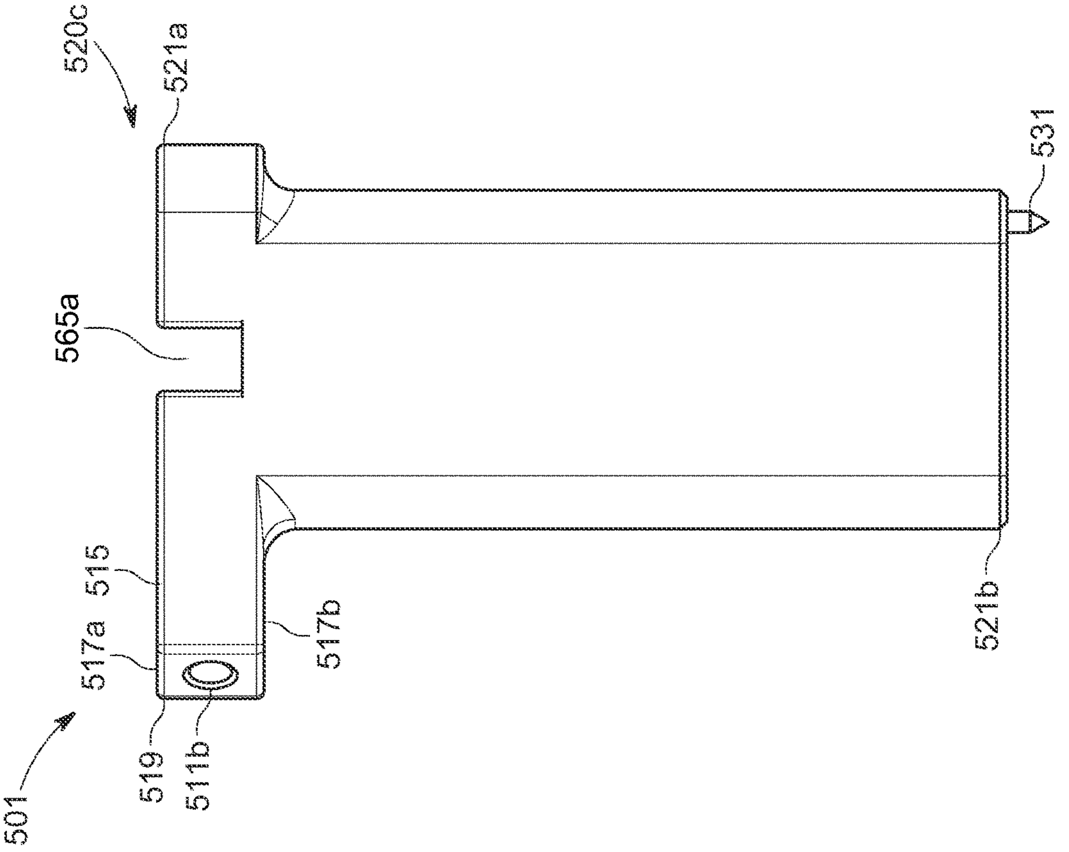
FIG. 7D is a front plan view of the drill guide base shown in FIG. 7A, in accordance with the invention.
Figure 7C:
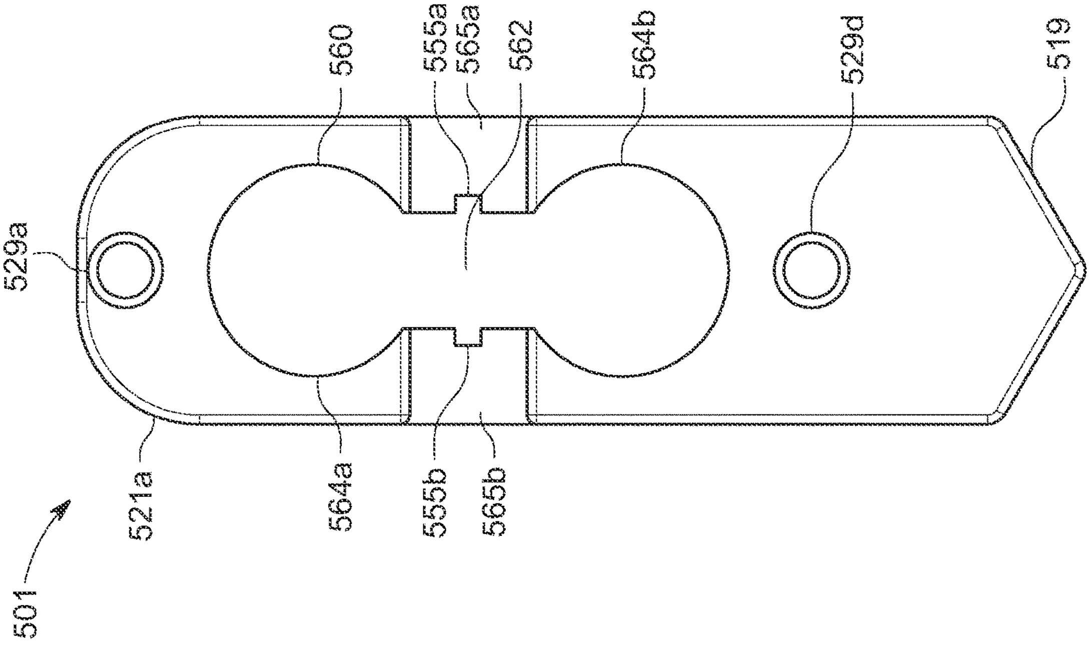
FIG. 7C is a top plan view of the drill guide base shown in FIG. 7A, in accordance with the invention.
Figure 7F:
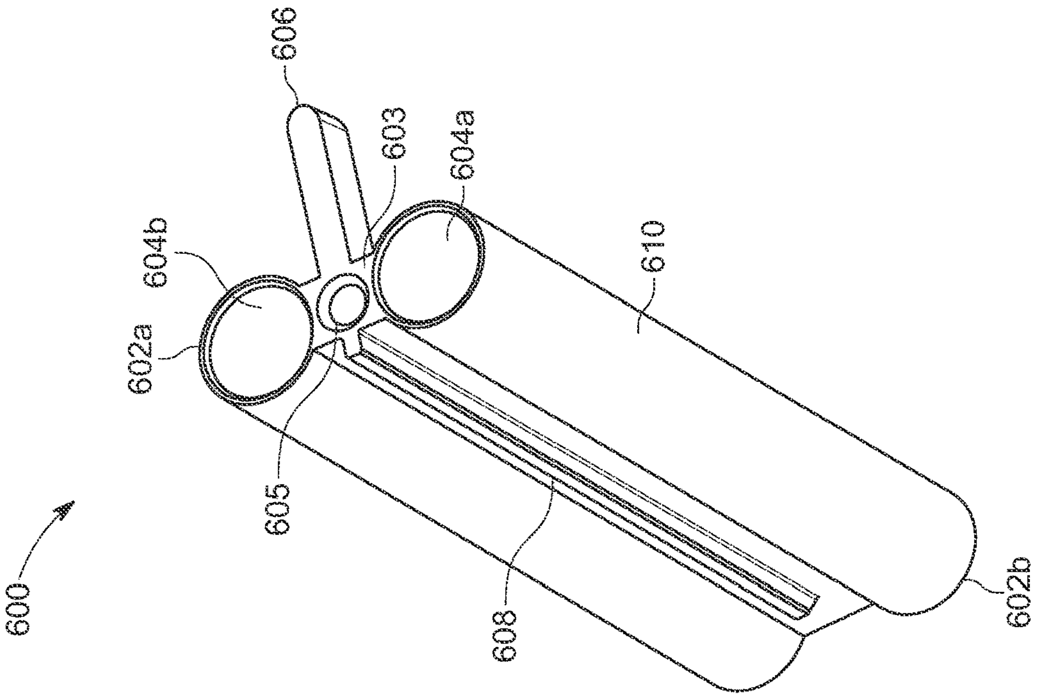
FIGS. 7E and 7F are perspective views of the drill guide insert shown in FIG. 7A.
Figure 7E:
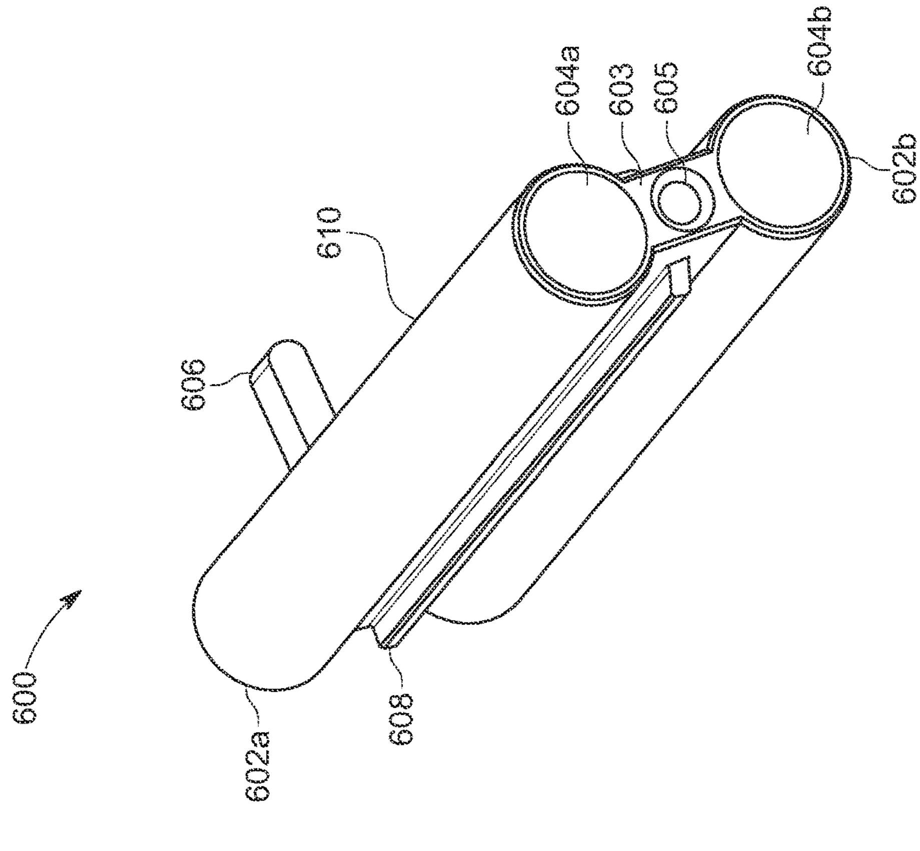

As illustrated in FIG. 7A, the drill guide assembly (also referred to herein as a "drill guide") 500 generally comprises a drill guide base 501, a bone dislodging apparatus; preferably, drill bit 700, and a drill guide insert 600, which is shown in FIGS. 7E and 7F.

According to the invention, the drill bit 700 can comprise drill bit 501*a*, 501*b* or 501*c* described in detail in priority U.S. application Ser. No. 17/833,960.

As illustrated in FIGS. 7B-7D, the drill guide base 501 comprises a proximal or top planar region 515, and proximal and distal ends 521*a*, 521*b* and two (2) K-wire lumens 529*a*, 529*d*.

As illustrated in FIGS. 7B and 7C, the drill guide base 501 further comprises two (2) K-wire lumens 529*a*, 529*d*, which extend from the proximal end 517*a* to the distal end 517*b* of the top planar region 515, i.e., extend through the top planar region 515. In a preferred embodiment, the K-wire lumens 529*a*, 529*d* are sized and configured to receive K-wires, such as K-wires 509, therein, as illustrated in FIG. 7B.

As illustrated in FIGS. 7B and 7D, the distal end 521*b* of the drill guide base 501 preferably comprises a pair of anchor members 531 that project from the distal end 521*b* of the drill guide base 501.

According to the invention, the anchor members 531 are designed and configured to pierce and, preferably, engage biological tissue to maintain a fixed position of the drill guide base 501 proximate thereto.

As further illustrated in FIGS. 7B and 7D, in a preferred embodiment, the proximal end 521*a* of the drill guide base 501 comprises an extended region 519, which comprises two (2) threaded holes 511*a* (not shown), 511*b*.

According to the invention, the threaded holes 511*a*, 511*b* are sized and configured to receive the threaded end of a drill guide handle, such as the threaded end 514 of the handle 510*a* described in priority U.S. application Ser. No. 17/833,960.

As illustrated in FIGS. 7A and 7C, the drill guide base 501 further comprises an internal drill guide insert opening 560, which, as discussed in detail below, is sized and configured to receive the drill guide insert 600 and the single-member bone structure prosthesis 70 and multi-member bone structure prostheses 170, 270 and 370 therein.

As further illustrated in FIGS. 7A and 7C, the drill guide insert opening 560 extends from the proximal end 521*a* to the distal end 521*b* of the drill guide base 501 and comprises a "dogbone" or "bi-lobe" cross-sectional shape comprising contiguous first and second lobe portions 564*a*, 564*b* connected by a medial portion 562. The drill guide insert opening 560 further comprises two (2) opposing guide channels 555*a*, 555*b* that are sized and configured to receive the guide rail 608 of drill guide insert 600 shown in FIGS. 7A, 7E, and 7F. The guide channels 555*a*, 555*b* are further configured to allow the guide rail 608 of drill guide insert 600 to slidably translate therethrough.

As illustrated in FIG. 7C, in a preferred embodiment, the medial portion 562 of the drill guide insert opening 560 is sized and configured to receive the center portion 603 of the drill guide insert 600.

As illustrated in FIGS. 7C and 7D, the drill guide base 501 further comprises receiving slots 565*a*, 565*b* proximate the proximal end 521*a* thereof that are sized and configured to receive and seat the extended region 606 of the drill guide insert 600, as illustrated in FIG. 7B and discussed below.

As illustrated in FIGS. 7E and 7F, the drill guide insert 600 comprises an elongated bi-luminal or "double-barrel" structure 610 that comprises first and second drill guide insert lumens 604*a*, 604*b* that are sized and configured to receive and position a drill bit, e.g., drill bit 700.

According to the invention, the first and second drill guide insert lumens 604*a*, 604*b* can be sized and configured to receive and position various sizes of drill bits to create various sizes of pilot SI joint openings.

In some embodiments of the invention, the drill guide further comprises a drill alignment pin, K-wire member and temporary fixation pin, such as alignment pin 532, K-wire member 552 and temporary fixation pin 533 described in U.S. application Ser. No. 17/833,960. In such embodiments, the first and second drill guide insert lumens 604*a*, 604*b* are further sized and configured to receive the drill alignment pin, temporary fixation pin and K-wire pin member therein.

As further illustrated in FIGS. 7B and 7C, the drill guide insert 600 further comprises a guide pin lumen 605, which, as illustrated in FIG. 7B, is sized and configured to receive a guide pin therethrough, such as guide pin 400 described in U.S. application Ser. No. 17/833,960.

As further illustrated in FIGS. 7B and 7C, the drill guide insert 600 further comprises an extended region or member (i.e., a handle) 606 that extends outwardly in a perpendicular direction relative to a longitudinal axis of the drill guide insert 600, and an integral guide rail 608 that is sized and configured to engage and slidably translate through the guide channels 555*a*, 555*b* of the drill guide base 501.

In a preferred embodiment, the extended member 606 is sized and configured to be received and seated in the receiving slots 565*a*, 565*b* of the drill guide base 501, as illustrated in FIG. 7B.

According to one invention of the invention, there is thus provided a method of stabilizing a dysfunctional SI joint comprising the following steps:

(i) providing drill guide 500;

(ii) providing multi-member bone structure prosthesis 270;

(iii) creating an incision proximate the dysfunctional SI joint, as set forth in U.S. application Ser. No. 17/833,960;

(iv) advancing a guide pin, such as guide pin 400, via a posterior approach through the incision and into the dysfunctional SI joint;

(v) positioning the drill guide insert 600 in the base 501 of the drill guide 500;

(vi) advancing the guide pin into and through the guide lumen 605 of the drill guide insert 600;

(vii) securing the drill guide 500 to the subject proximate the dysfunctional SI joint via K-wires, such as described in connection with drill guide 520*c* in U.S. application Ser. No. 17/833,960;

(viii) creating the ilium portion of the pilot SI joint opening as set forth in U.S. application Ser. No. 17/833,960;

(ix) advancing the first elongated member 276*a* of the multi-member bone structure prosthesis 270 to and into the ilium portion of the pilot SI joint opening created by the drill guide;

(x) creating the sacrum portion of the pilot SI joint opening as set forth in U.S. application Ser. No. 17/833,960;

(xi) advancing the second elongated member 276_b_ of the multi-member bone structure prosthesis 270 to and into the sacrum portion of the pilot SI joint opening created by the drill guide;

(xii) removing the drill guide insert 600 from the base 501 of the drill guide 500;

(xiii) advancing the guide pin into and through the guide lumen 201 of the central member 200;

(xiv) advancing the central member 200 to the dysfunctional SI joint and proximate the first and second elongated members 276_a_, 276_b;_

(xv) slidably securing the central member 200 to the first and second elongated members 276_a_, 276_b_ by inserting the first and second discontinuous rails 224_a_, 224_b_ of the central member 200 into the rail slots 225_a_, 225_b_ of the first and second elongated members 276_a_, 276_b;_

(xvi) advancing the central member 200 into the dysfunctional SI joint to a desired position;

(xvii) removing the base 501 of the drill guide 500 from the subject's body;

(xviii) extracting the guide pin out of the dysfunctional SI joint; and (xix) closing the incision.

In a preferred embodiment, the guide pin, such as guide pin 400, is advanced via an inferior-posterior trajectory through the incision and into the dysfunctional SI joint.

As will readily be appreciated by one having ordinary skill in the art, the present invention provides numerous advantages compared to prior art systems and methods for stabilizing dysfunctional SI joints. Among the advantages are the following:

the provision of minimally-invasive SI joint stabilization systems and apparatus, and methods of using same, which facilitate inferior-posterior trajectory placement of single-member and multi-member bone structure prostheses in dysfunctional SI joints and, thereby, stabilization of the dysfunctional SI joints;

the provision of minimally-invasive SI joint stabilization systems and apparatus, which, when employed to stabilize dysfunctional SI joints, disrupt less tissue and muscles, and avoid nerves and large blood vessels;

the provision of improved minimally-invasive SI joint stabilization systems and apparatus, which, when employed to stabilize dysfunctional SI joints, effectively ameliorate pain associated with SI joint dysfunction;

the provision of single-member and multi-member bone structure prostheses that can readily be employed in minimally-invasive SI joint stabilization methods;

the provision of single-member and multi-member bone structure prostheses that effectively stabilize dysfunctional SI joints; and the provision of single-member and multi-member bone structure prostheses that facilitate remodeling of damaged osseous tissue and regeneration of new osseous tissue and osseous tissue structures.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An apparatus for stabilizing a dysfunctional sacroiliac (SI) joint, said apparatus comprising:

a multi-member structure comprising a first elongated member, a second elongated member and an osteotome member, said first elongated member comprising a first open proximal end, a first closed distal end and a first osteotome engagement region disposed between said first open proximal end and said first closed distal end of said first elongated member, said first osteotome engagement region comprising a first rail slot, said first elongated member further comprising a first internal lumen that extends from said first open proximal end to said first closed distal end of said first elongated member, said second elongated member comprising a second open proximal end, a second closed distal end and a second osteotome engagement region disposed between said second open proximal end and said second closed distal end of said second elongated member, said second osteotome engagement region comprising a second rail slot, said second elongated member further comprising a second internal lumen that extends from said second open proximal end to said second closed distal end of said second elongated member, said first elongated member and said second elongated member comprising hollow, fenestrated structures, said osteotome member comprising a longitudinal axis, a third open proximal end, a first open distal end, a first outer surface region and an opposing second outer surface region, said first outer surface region of said osteotome member comprising a first osteotome member rail section sized and configured to engage said first rail slot of said first elongated member therein, wherein said first elongated member is coupled to said osteotome member, said second outer surface region of said osteotome member comprising a second osteotome member rail section sized and configured to engage said second rail slot of said second elongated member, wherein said second elongated member is coupled to said osteotome member, said osteotome member further comprising an elongated osteotome opening disposed between said third open proximal end and said first open distal end of said osteotome member and extending through said osteotome member, said elongated osteotome opening, when said first elongated member and said second elongated member are said coupled to said osteotome member, in communication with said first internal lumen of said first elongated member and said second internal lumen of said second elongated member, wherein said multi-member structure comprises a continuous structure opening, said osteotome member further comprising a tapered region disposed on said first open distal end of said osteotome member, said tapered region comprising a gradually decreasing thickness along said longitudinal axis of said osteotome member.

2. The apparatus of claim 1, wherein, when said first elongated member is said coupled to said osteotome member and said second elongated member is said coupled to said osteotome member, said osteotome member is disposed between said first elongated member and said second elongated member, wherein said first elongated member, said osteotome member and said second elongated member are positioned on a common lateral plane.

3. The apparatus of claim 1, wherein said first internal lumen of said first elongated member is adapted to receive a first osteogenic composition therein.

4. The apparatus of claim 3, wherein said first osteogenic composition comprises a first bone material selected from the group consisting of demineralized bone matrix, autograft bone material, allograft bone material and xenograft bone material.

5. The apparatus of claim 3, wherein said first osteogenic composition comprises a first bone morphogenic protein (BMP) selected from the group consisting of BMP-1, BMP2a, BMP2b, BMP3, BMP4, BMP5, BMP6, BMP7 and BMP8a.

6. The apparatus of claim 1, wherein said first elongated member further comprises a first plurality of slots in communication with said first internal lumen.

7. The apparatus of claim 1, wherein said second internal lumen of said second elongated member is adapted to receive a second osteogenic composition therein.

8. The apparatus of claim 7, wherein said second osteogenic composition comprises a second bone material selected from the group consisting of demineralized bone matrix, autograft bone material, allograft bone material and xenograft bone material.

9. The apparatus of claim 7, wherein said second osteogenic composition comprises a second bone morphogenic protein (BMP) selected from the group consisting of BMP-1, BMP2a, BMP2b, BMP3, BMP4, BMP5, BMP6, BMP7 and BMP8a.

10. The apparatus of claim 1, wherein said second elongated member further comprises a second plurality of slots in communication with said second internal lumen.

11. The apparatus of claim 1, wherein said osteotome member further comprises a first guidewire lumen that extends from said third open proximal end of said osteotome member to said elongated osteotome opening and a second guidewire lumen that extends from said first open distal end of said osteotome member to said elongated osteotome opening, said first guidewire lumen and said second guidewire lumen aligned, sized and configured to receive a guide pin into and though said first and second guidewire lumens.

12. The apparatus of claim 1, wherein said first elongated member and said second elongated member comprise porous structures.

* * * * *